US012106849B2

(12) United States Patent
Hopkins

(10) Patent No.: US 12,106,849 B2
(45) Date of Patent: Oct. 1, 2024

(54) DIGITAL DATA TASK STATIONS RECONFIGURING DATA CONNECTION POINTS

(71) Applicant: Heather Hopkins, Lexington, SC (US)

(72) Inventor: Heather Hopkins, Lexington, SC (US)

(73) Assignee: Heather Hopkins, Lexington, SC (US)

( * ) Notice: Subject to any disclaimer, the term of this patent is extended or adjusted under 35 U.S.C. 154(b) by 465 days.

(21) Appl. No.: 17/398,769

(22) Filed: Aug. 10, 2021

(65) Prior Publication Data

US 2022/0122720 A1 Apr. 21, 2022

Related U.S. Application Data

(60) Provisional application No. 63/092,390, filed on Oct. 15, 2020.

(51) Int. Cl.
*G16H 40/20* (2018.01)

(52) U.S. Cl.
CPC .................. *G16H 40/20* (2018.01)

(58) Field of Classification Search
CPC ........ G16H 40/67; G16H 30/20; G16H 10/60; G16H 50/20; G16H 40/20
See application file for complete search history.

(56) References Cited

U.S. PATENT DOCUMENTS

2009/0112614 A1 4/2009 Guimaraes
2021/0100643 A1* 4/2021 Weiss ....................... G06N 3/08

FOREIGN PATENT DOCUMENTS

WO WO-2008149222 A2 * 12/2008 ............... A61C 7/00

OTHER PUBLICATIONS

Brown, Andrew D., and Thomas R. Marotta. "Using machine learning for sequence-level automated MRI protocol selection in neuroradiology." Journal of the American Medical Informatics Association 25.5 (2018): 568-571. (Year: 2018).*
International Search Report and Written Opinion from corresponding International Appln. No. PCT/US2021/045363 dated Nov. 4, 2021.
International Preliminary Report on Patentability from counterpart International Application No. PCT/US2021/045363, dated Apr. 27, 2023.

* cited by examiner

*Primary Examiner* — Jason B Dunham
*Assistant Examiner* — Constantine Siozopoulos
(74) *Attorney, Agent, or Firm* — DLA Piper LLP (US)

(57) ABSTRACT

A first data task station which has a first predetermined data content requirement. A data content receiver receives data content. A first activator enables the data content receiver through a data intake of data task station, to associate with a first data content. Movement of the first data content to an automator site of the first data task station, actuates the screener. A second activator of the computer, by operation of the automator, enables, after the first pre-determined data content satisfies the screen against said first pre-determined data content requirement, a second data task station associated with a second predetermined data content requirement. A disabler, by operation of the automator, after the first pre-determined data content satisfies the screen against the first pre-determined data content requirement, disables the further screen of the first data content of said first data station.

16 Claims, 11 Drawing Sheets

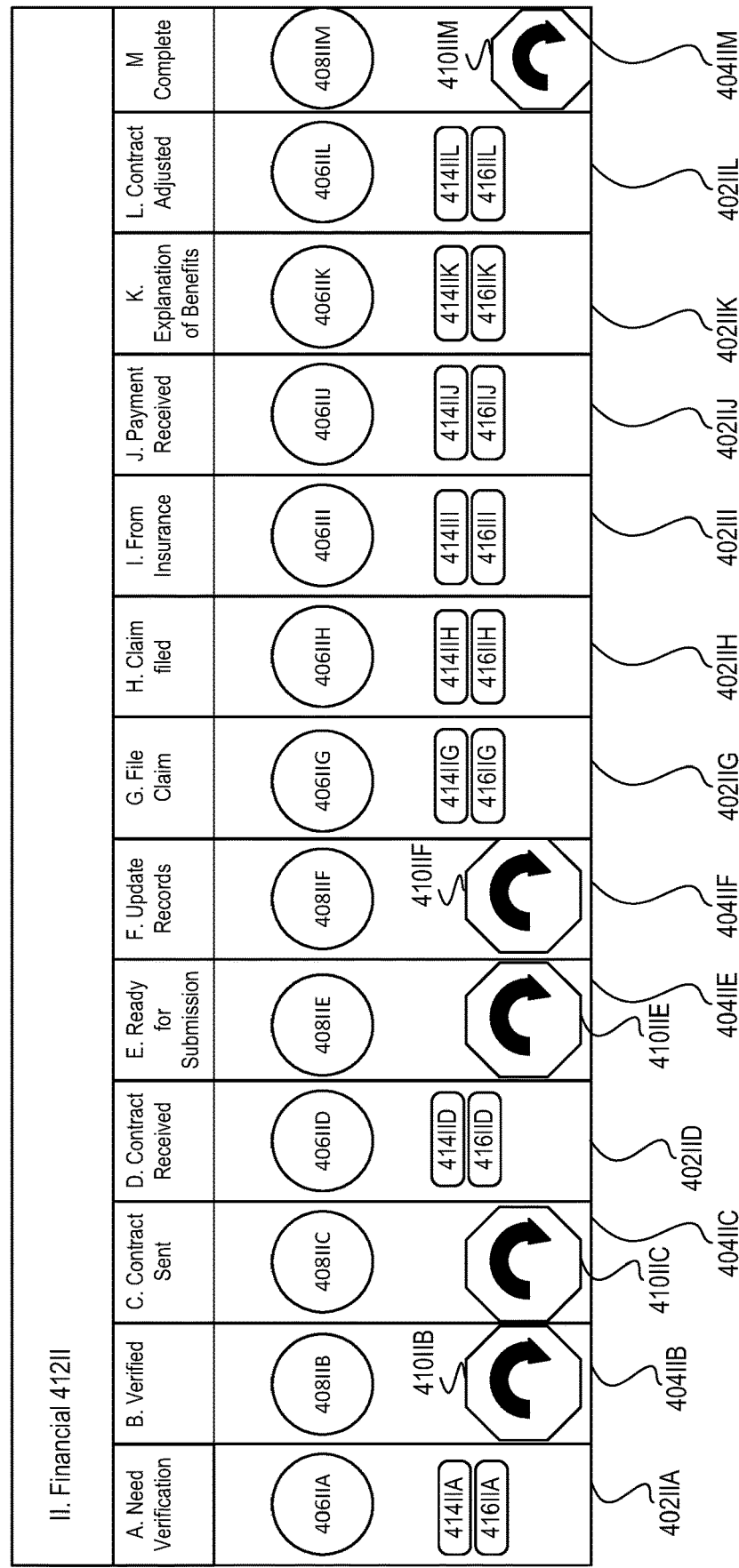
FIG. 4B1

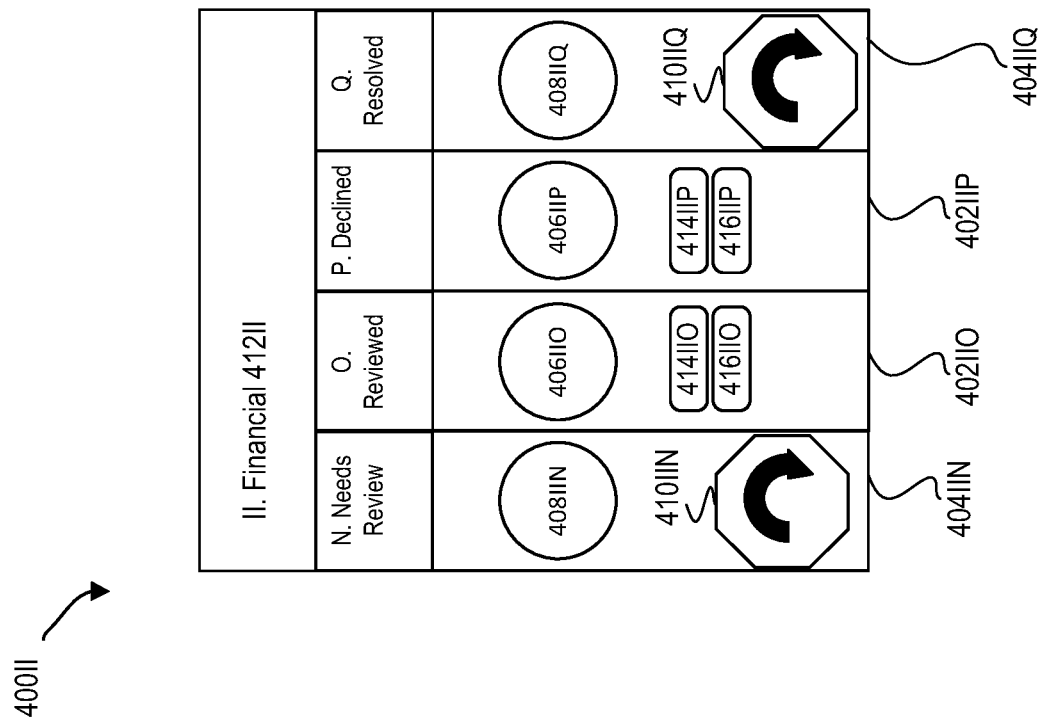
FIG. 4B2

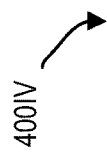
FIG. 4D1

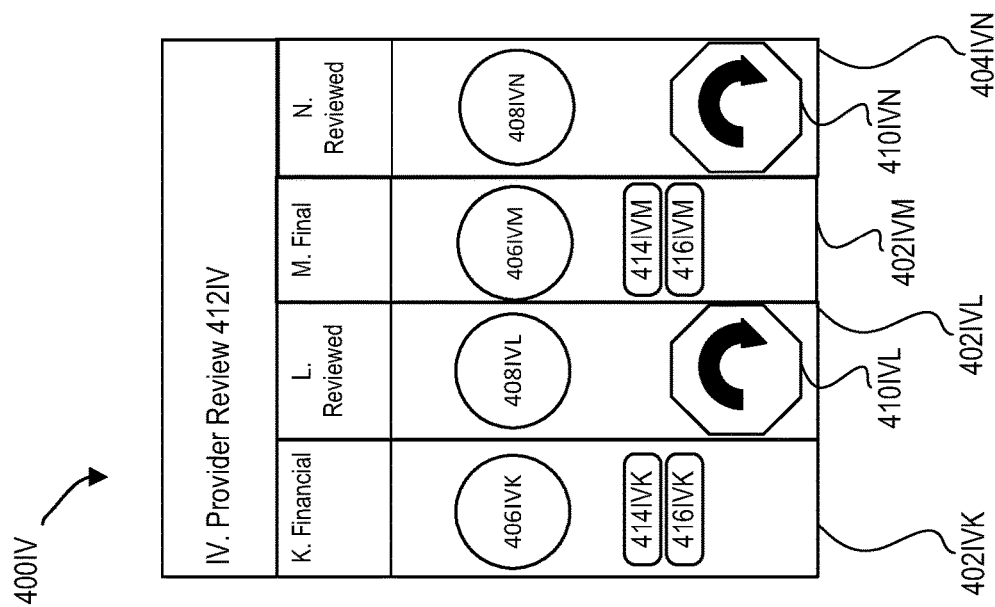
FIG. 4D2

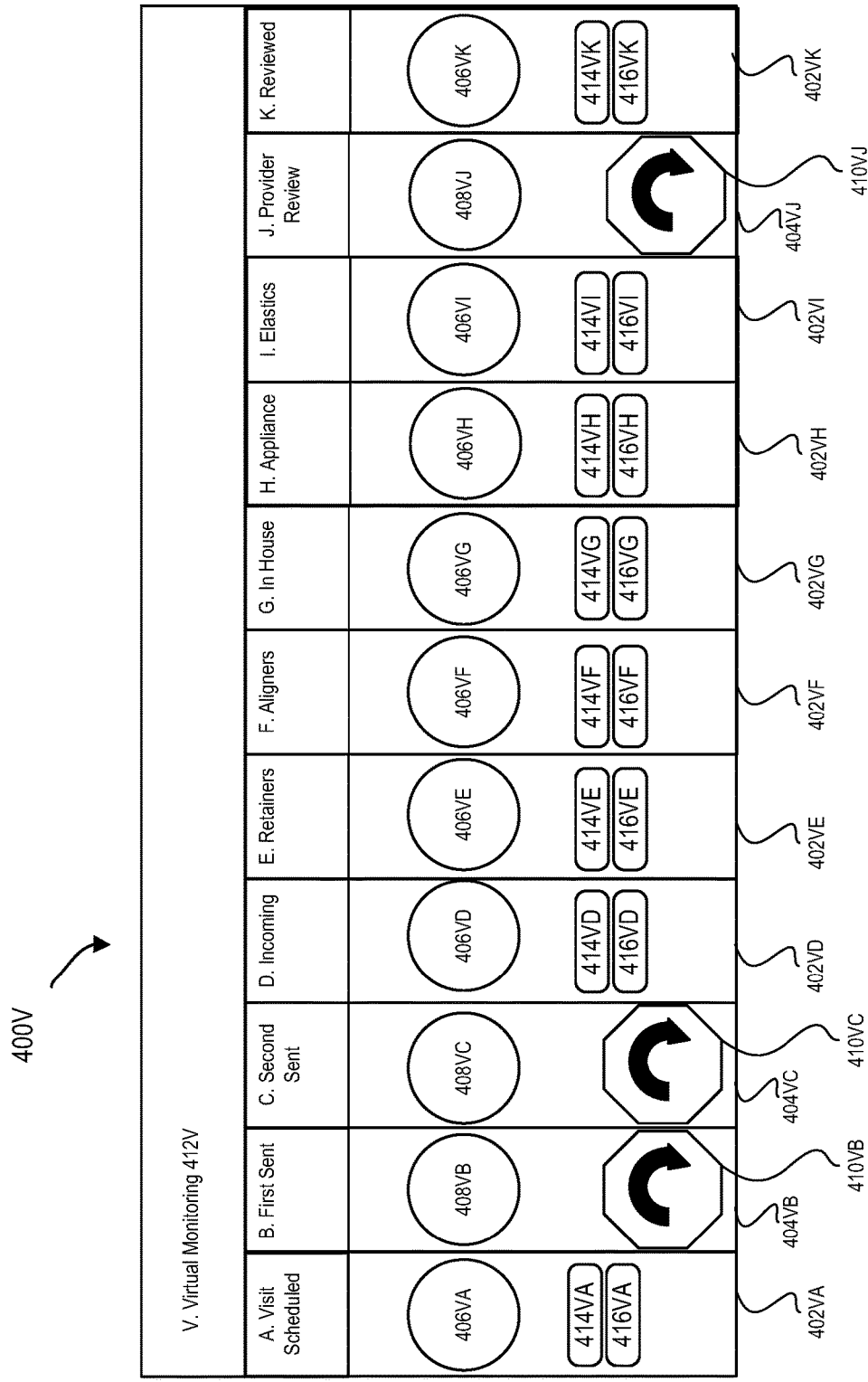
FIG. 4E1

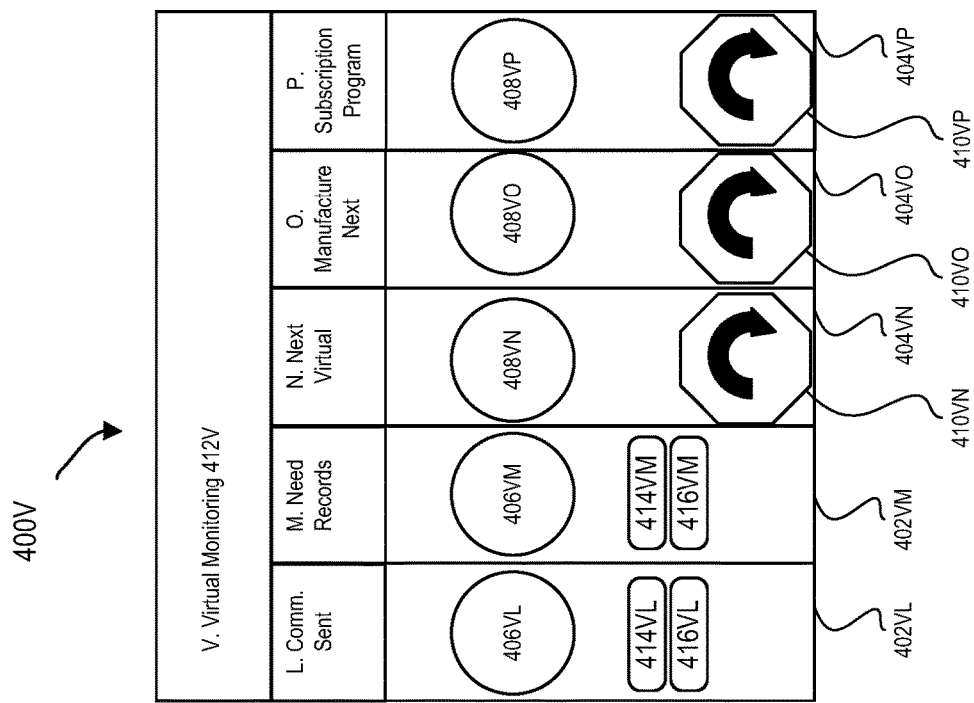
FIG. 4E2

DIGITAL DATA TASK STATIONS RECONFIGURING DATA CONNECTION POINTS

FIELD

The present disclosure is generally directed to a computer implemented system which includes a graphical user interface having an array of interactive data processing stations which themselves include interactive connections within and between the processing stations.

BACKGROUND

Isolated teams, poor coordination, and limited lateral communication hinder innovation and growth within most organizations. Processes and strategies are often developed in silos. Decision making is fragmented and compartmentalized, leading to obscurity around objectives for products, services, or target markets. Teams end up duplicating efforts and wasting resources. Efficiency, quality control, and resource allocation are all inhibited when this occurs.

Many projects or problems require a multi-dimensional approach that requires many decision makers to weigh multiple variables before a valuable contribution can be made. Often, each decision maker may specialize in a certain area of knowledge. When a process involves multi-criteria decision making, simultaneous decisions across multiple teams can be counterproductive. For example, teams may be making decisions on information that is out of date. As a result, in situations where each decision is prerequisite in chain of decisions, this issue may compound, thus leading to an increase in errors. Organizations across a wide range of sectors, including, but not limited to research and development, manufacturing, sales, distribution and logistics, healthcare, professional services and the like, suffer when interdepartmental and/or intradepartmental decisions are made simultaneously without visibility across an organization.

For example, during product development, engineers, marketing teams, sales teams, legal teams, and the end user may all have different priorities when contributing to a new product: engineers may focus on manufacturing costs and reproducibility as a priority; marketing teams may focus on creating simple, easy-to-interpret visual representations as a priority; sales teams may focus on improvements the product may bring to the market; ;legal teams may focus on risk mitigation; and. the end user may focus on efficiency. If all of these teams are working in parallel, and are also blind to the perspective, expertise, and efforts of each other, their attempts to bring a valuable product to market in a timely, cost effective manner may be greatly impeded.

In another example, an organization may be trying to onboard a new customer or client. Such process may involve an intake specialist, an account auditor, training specialist, financial coordinator and the like. If all of these teams are trying to contact a new customer or client concurrently, resources and payroll hours are wasted. These teams may not only be duplicating efforts, but they may also actually deter the client or customer from completing onboarding due to lack of efficiency during the process.

The construction industry is full of decisions which require multiple factors to be considered. For example, a contractor may be trying to compare price, quality, and availability of materials along with price, quality, and availability of labor all while trying to work within a strict timeline. Extra costs may be spent to rush items, only to later realize there is no labor available. Higher quality items may be substituted for lower grade, in an attempt to save time and/or cost. Upon arrival, these lower grade items may not be compatible with already installed items.

Another example of a sector which is plagued by inefficiencies and redundancies is healthcare. Having the appropriate information to make a timely decision can mean the difference between life or death. Currently, healthcare providers may only have access to out of date or incomplete records when making a decision on patient care due to segregation of data. Information added to a patient chart in a non-sensical order may also have a negative impact on a treatment decision. Diagnostic testing, lab orders, prescriptions, clinical records, insurance information, demographic information, and health history may all be segregated and updated independently. This is destructive to the level of continuity of care a healthcare provider is able to provide.

In all of the above examples, a lack of real-time operating information creates inefficiencies, loss of time, increased costs, and a greater margin for error. The following disclosure presents an improvement to current systems.

In all of the above examples, individuals, teams, departments, and/organizations tend to have a point person or project manager who manages a group of these compartmentalized teams. Each project manager may be responsible for a specific project which may be one of many when taking a global view. Project managers may also be in charge of managing a team with specialized training to complete a specific portion of a project. Even though individual projects may have oversight at a local level, there tends to be a lack of centralized information and oversight at an organizational level. For example, a patient may have a diagnostic and treatment planning consultation with a healthcare provider for an elective procedure. The patient may wait six months before calling the office back to schedule the procedure. A scheduler may only have access to see what appointment type should be scheduled next. The scheduler may schedule the procedure for the patient. When reviewing the schedule, a healthcare provider does may not have access to easily view when the previous appointment took place, review the diagnostic records obtained, and/or review any financial information. A financial or insurance coordinator may have reviewed insurance coverage at the initial consultation but receives no notification when a patient schedules to review this information again.

The scheduler is operating off outdated information when scheduling the appointment. A healthcare provider may be working off incomplete information when reviewing a daily schedule. When the patient arrives for the procedure, it may be discovered that new diagnostic testing is needed, a completely different procedure is now needed due to a change in the patient's diagnosis, and/or the patient's insurance is no longer valid. Due to this lack of communication and no real time operating information valuable time and resources have been lost. The patient is most likely upset and may decline treatment at this point.

One or more techniques described herein provide several advantages over the foregoing techniques. For example, to account for incomplete patient information, the present system may display real-time operating information to the appropriate user at the appropriate time. In this manner, a healthcare provider would no longer have to search through multiple sources or reach out to multiple departments to check for any informational updates. Instead, the present system may provide the data record to a healthcare provider once all up-to-date information has been collected.

Healthcare operating systems do not allow for records to be reviewed and modified in a sequential order. For example, a healthcare provider may review a patient chart and make a treatment decision before all outstanding laboratory results have been received and entered. To account for this, the present system may utilize a combination of screeners and automators that control when, where, and how a patient chart is displayed to an authorized user. In this example, the present system provides improvements over conventional healthcare operating systems by preventing a healthcare professional from making treatment decisions without first reviewing information critical to the treatment decisions (e.g., what laboratory tests are still outstanding, the expected time and date for test results to be complete and visible within the patient chart, and the like). In this manner, the healthcare provider may have all requisite information to correctly make the treatment decision (e.g., weigh the risk benefit of administering treatment to a patient versus waiting for the outstanding laboratory results).

Current office management systems within healthcare do not offer the ability to track and manage steps that do not require physical visits. If a patient needs a follow up call, it is up to office staff to remember to do this. If a patient needs a prescription sent to a pharmacy, a clinical technician must remember to send it. The present system eliminates this onus by automating, receiving, and displaying patient communication to the appropriate employee. For example, the present system may automate due dates, automatically send data to external systems, automatically provide status updates, automatically assign a patient chart to a specific employee, and the like.

Conventional project management programs require a project manager to oversee a team and monitor where the project is in real-time. All aspects of the project may be visible to the project manager, such as, but not limited to, budgets running low, deadlines not being met, or other any other issues which may arise while managing a project, may be monitored. The present system improves upon traditional project management by eliminating the need for a project manager to track and oversee every step. To do so, the present system utilizes a combination of data processing stations, screeners, and automators to move and/or pass data along sequentially, while collecting all necessary information in accordance with a configured timeline. If, for example, a data record is delayed at a data task station, notifications may be sent, the present system may alert a universal administrator. Thus, the improvements offered by the present system eliminate any need for a project manager to micromanage a project. Instead, if a project is not meeting a requirement, automators will notify a project manager and all relevant information will be displayed to address the issue, before any opportunity for a deadline to be missed.

SUMMARY

Naturally, further advantages of the present disclosure are disclosed throughout other areas of the specification, drawings, photographs, and claims.

In some embodiments, a computer-implemented system for implementing and tracking a healthcare process is disclosed herein. The computer-implemented system includes a processor communicatively coupled to a non-transitory memory containing a computer code. The computer code, when executed by the processor, performs operations. The operations include enabling a first data task station associated with a first pre-determined data content requirement. The first data task station is associated with at least a first step of a healthcare process. The operations further include enabling a data content receiver to receive, through a data intake of said first data task station, a first data content. The operations further include associating said first data content with said data content receiver through said data intake of the first data task station. The operations further include screening said first data content associated with said data content receiver against the first pre-determined data content requirement of said first data task station. The screen us actuated by movement of said first data content associated with said data content receiver to an automator site of said first data task station, said automator site includes an automator. The operations further include enabling, by operation of said automator, after said first data content satisfying said screen against said first pre-determined data content requirement, a second data task station associated with a second predetermined data content requirement. The second data task station is associated with at least a second step of the healthcare process. The operations further include enabling, by operation of said automator, said data content receiver to receive second data content through a data intake of said second data task station. The operations further include disabling, by operation of said automator, after said first data content satisfying said screen against said first pre-determined data content requirement, the screen of said first data content of said first data task station.

In some embodiments, a computer system is disclosed herein. The computer system has an operating state wherein, in said operating state, said computer system is configured to perform operations. The operations include screening a first data content associated with a data content receiver against a first pre-determined data content requirement of a first data task station. The screen is actuated by movement of said first data content of said first data task station to an automator site of said first data task station including an automator, wherein the first data task station is associated with a first step of a healthcare process. The operations further include enabling, by operation of said automator, after said first data content satisfying said screen against said first pre-determined data content requirement, a second data task station associated with a second predetermined data content requirement. The second data task station is associated with a second step of the healthcare process. The operations further include disabling, by operation of said automator, after said first data content satisfying said screen against said first pre-determined data content requirement, the screen of said first data content of said first data task station.

In some embodiments, a method in a computer implemented system is disclosed herein. A first data task station associated with a first pre-determined data content requirement is enabled. A data content receiver is enabled to receive, through a data intake of said first data task station, a first data content. The first data task station is associated with a first step of a healthcare process. The first data content is associated with said data content receiver through said data intake of the first data task station. The first data content associated with said data content receiver is screened against the first pre-determined data content requirement of said first data task station. The screen is actuated by movement of said first data content associated with said data content receiver to an automator site of said first data task station, said automator site includes an automator. After said first data content satisfying said screen against said first pre-determined data content requirement, a second data task station associated with a second pre-determined data content requirement is enabled by operation of said automator. The second data task station is associated with a second step of the healthcare process. The data content receiver is enabled, by operation of said automator, to receive second data content through a data intake of said second data task station. After said first data content satisfying said screen against said first pre-determined data content requirement, the screen of said first data content of said first data task station is disabled by operation of said automator.

In some embodiments, a computing system is disclosed herein. The computing system includes a first data task station, a data content receiver, a first activator, an aggregator, a screener, a second activator, and a disabler. The first data task station has a first pre-determined data content requirement. The first data task station is associated with a first step of a healthcare process. The data content receiver receives data content. The first activator enables said data content receiver through a data intake of said first data task station to associate with a first data content. The aggregator associates said first data content with said data content receiver through said data intake of the first data task station. The screener, which, upon actuation, screens said first data content associated with said data content receiver against said first pre-determined data content requirement, movement of said first data content to an automator site of said first data task station, actuates said screener, said automator site having an automator. The second activator, by operation of said automator, enables, after said first data content satisfying said screen against said first pre-determined data content requirement, a second data task station associated with a second pre-determined data content requirement, wherein the second data task station is associated with a second step of the healthcare process. The disabler, by operation of said automator, after said first data content satisfying said screen against said first pre-determined data content requirement, disables the screen of said first data content of said first data task station.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

FIGS. 4B1 and 4B2 illustrate an exemplary data task station, according to example embodiments.

FIGS. 4D1 and 4D2 illustrate an exemplary data task station, according to example embodiments.

FIGS. 4E1 and 4E2 illustrates an exemplary data task station, according to example embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Figure 1:
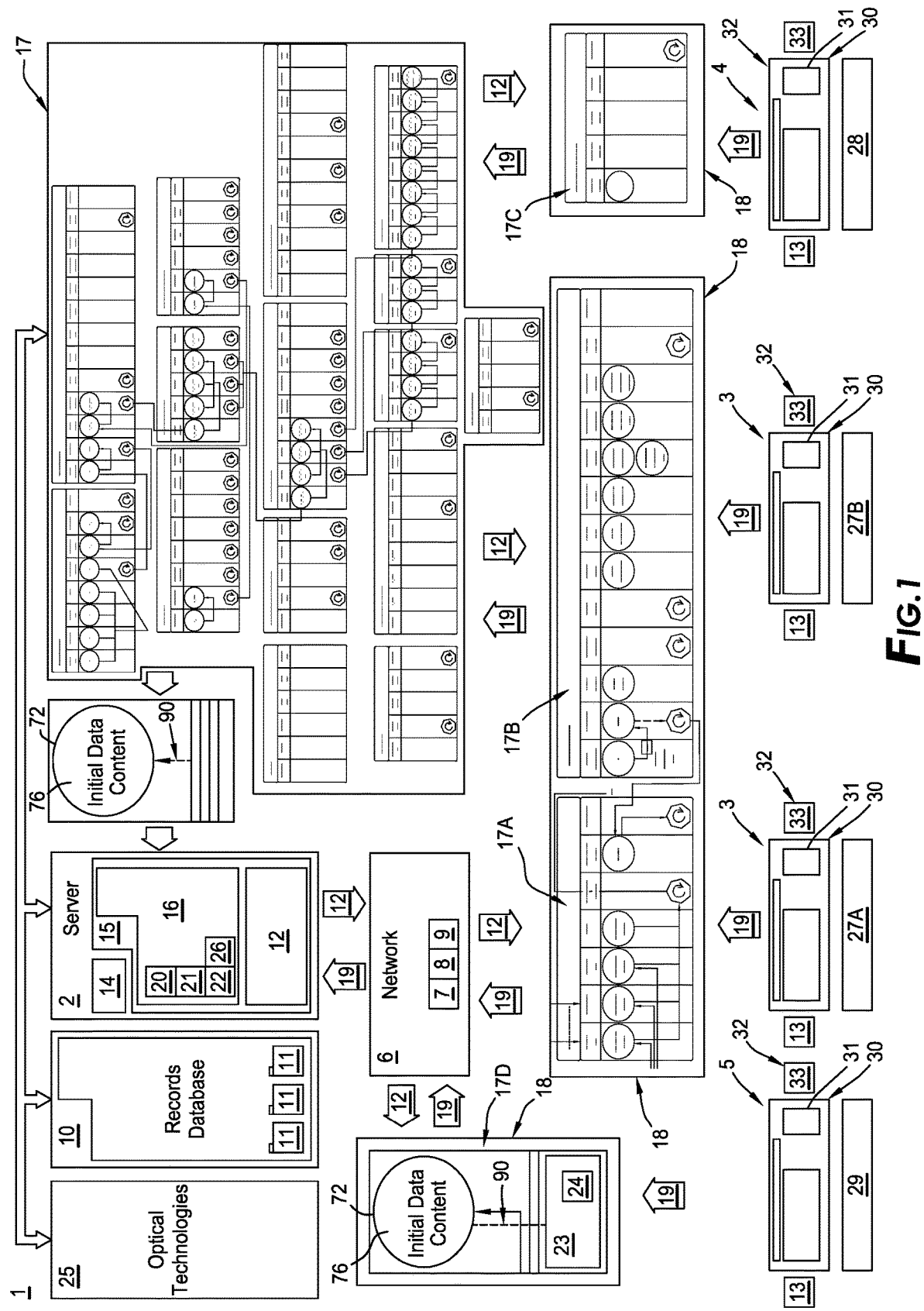
FIG. 1 is a block diagram of an interactive a computer implemented array internegative digital task stations, according to example embodiments.

One or more techniques described herein are generally directed to a system having an array of interactive data processing stations. In some embodiments, the array of interactive data processing stations may include interactive connections within and between the data task stations creating a central framework. Data may be centralized into one location as it moves through a non-linear sequential process, which may include many possible pathways based on pre-determined data requirements at each step. Depending on which set of requirements is met, the aggregated data may move to the appropriate data task station by the operation of an automator.

The present system provides several advantages over conventional techniques. These advantages include presenting only relevant data to authorized users. Additionally, a unique data request may be displayed only to an authorized user with the training and access to collect and add the requested information. An authorized user may then pass this information along to an Automator. An automator may screen this information against a predetermined data requirement. If the requirement is met the data record may be transferred. The data record may now be visible by a different authorized user. Only the data relevant to this authorized user may be displayed, along with a unique data request. Upon review, an authorized user with training and access to collect the requested information. After completion an authorized user may transfer the data record to an automator. The automator may screen this information against a predetermined data requirement. If the requirement is not met, the data record may remain visible to the authorized user until the appropriate data requirement has been met.

Conventionally, the process for contacting, scheduling, evaluating, arranging financials, filing insurance, and preparing treatment for a consumer or new patient in the healthcare setting is bulky and time consuming. As those skilled in the art understand, multiple parties may need to gain access to certain patient or client information, at times multiple departments may be working concurrently to obtain information from the same sources leading to wasted time and increase in error For example, patient or client information may need to be provided or passed to administrative staff, medical staff, dental staff, insurance agencies, third party providers (e.g., dental laboratory), imaging specialists (e.g., x-rays, MRIs, CAT scans, etc.), and the like. Without a proper structure, steps in the process are easily skipped, delayed, or done incorrectly leading to delayed or inappropriate treatment.

To account for this, one or more techniques described herein provides an improved system that utilizes an array of interactive data task stations that may include interactive connections within and between task stations. In some embodiments, each task station or set of task stations may be selectively enabled/disabled depending on where the state of the healthcare process. Further, in some embodiments, each party to the procedure may be provided with a different set of interactive data task stations. In some embodiments, these different sets of interactive data task stations may include interactive connections between sets of interactive data task stations. Such interactive connections may allow any party to the process (e.g., a healthcare process) to identify where a data record is in process and what party is currently assigned to an associated action. In this manner, a healthcare process may flow, seamlessly, between parties using the interactive connections within and between task stations, while maintaining knowledge about where a data record is within the healthcare process. Information may be passed between departments via an automator once the required information for a respective data task station has been entered. Such process eliminates the need for multiple departments to actively search for data records in need of action. Instead, as the data record moves throughout the process, all information is aggregated. For example, when an order is submitted to a laboratory all necessary information is included in the data record which then moves within and between data task stations. After the laboratory orders have been submitted, the data record may be moved to an automator, which may send or forward the information to a healthcare provider. A healthcare provider may view a data record only when action is needed, and a due date may be automatically populated. A complete history of the data record may be reviewed by a healthcare provider. This improves the speed and accuracy at which a healthcare provider may review real-time information needed to make treatment decisions.

Further, in some embodiments, one or more data task stations may include a checklist of items that may be or must be completed before progression to a following data task station. In this manner, the system may ensure that all necessary information is provided at each step of the healthcare process.

The System. Generally, with reference to FIGS. 1 through 4F, a computer implemented system 1 (also referred to as the "system 1") can be distributed on one or more servers 2 operably coupled to one or more client computing devices 3 or one or more service provider computing devices 4 or one or more patient computing devices 5 directly, or operably coupled to the client computing devices 3, the service provider computing devices 4 and the patient computing devices 5 by a public network 6, such as the Internet 7, a cellular-based wireless network(s) 8, or a local network 9 (individually or collectively the "network"). While the terms "client computing device" and "service provider computing device" and "patient computing devices" are utilized in association with certain embodiments, this is not intended to limit the scope of the disclosure to those particular embodiments, rather certain embodiments may generically include a first computing device, a second computing device 4 through n . . . computing devices operably coupled or communicating as above described (in the examples "arrows" indicating the operable coupling or communication). In some embodiments, the system 1 can further include a records database 10 from which records 11 can be retrieved by a request from any one of the client computing devices 3, the service provider computing devices 4, or the patient computing devices 5 to the extent the computing devices have system 1 or record database 10 access privileges to retrieve system content 12 including, but not limited to, records 11.

Figure 2:
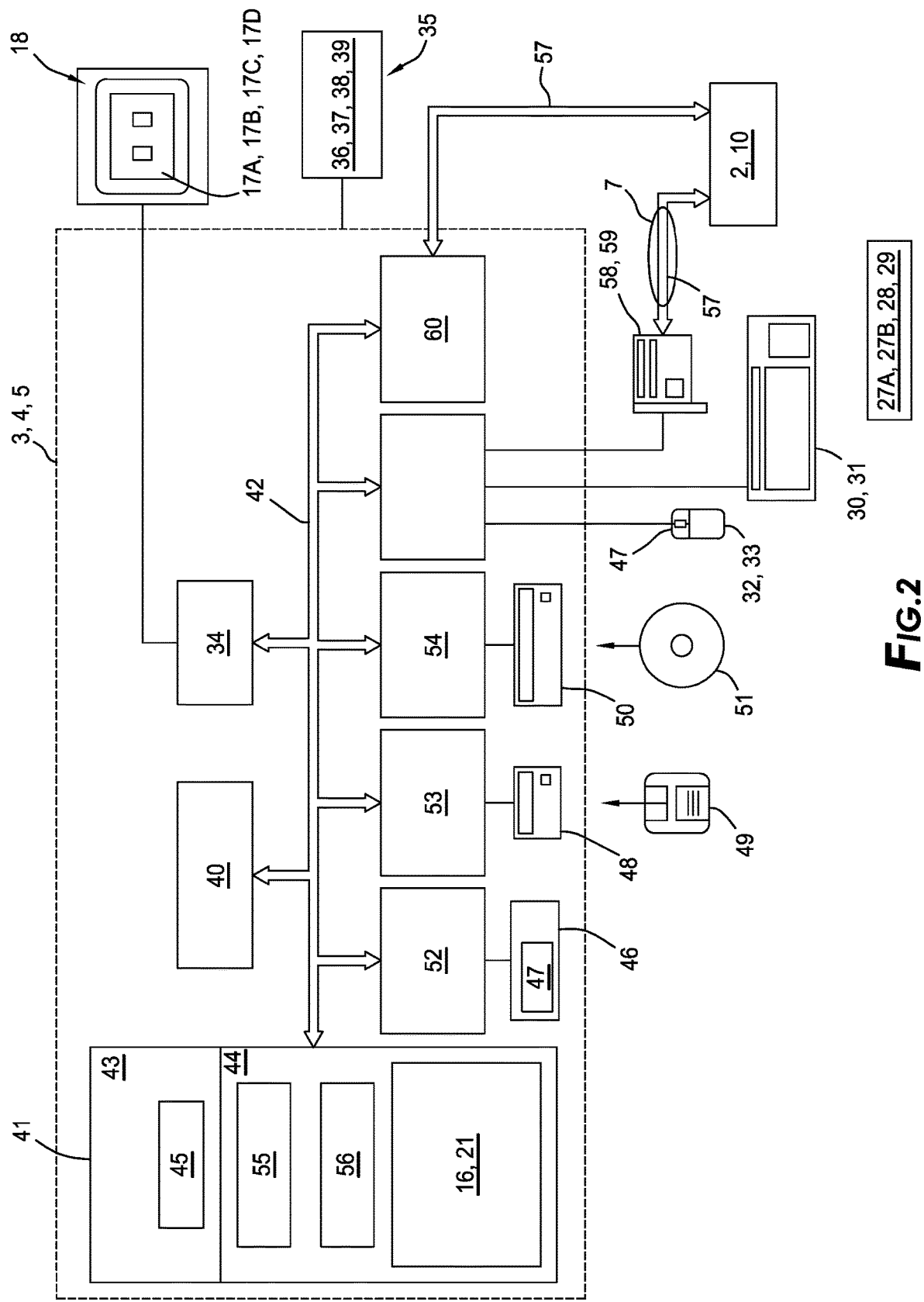
FIG. 2 is a block diagram of an illustrative computer means, network means and computer readable medium which provides computer-executable instructions to provide an embodiment of the computer implemented array of interactive digital task stations, according to example embodiments.

Again, with primary reference to FIGS. 1 and 2, depicting illustrative computer hardware, network elements, and computer readable media which can be utilized to practice embodiments of the system 1. It is not intended that embodiments of the disclosure be practiced in only wide area computing environments or only in local computing environments, but rather the disclosure can be practiced in local computing environments or in distributed computing environments where functions or tasks are performed by remote processing devices that are linked through a communications network. In a distributed computing environment, program modules may be located in both a local or in a remote memory storage device(s) or device elements.

Also while one or more embodiments of the disclosure may be described in the general context of computer-executable instructions such as an application program and program modules which utilize routines, programs, objects, components, data structures, or the like, to perform particular functions or tasks or implement particular abstract data types, or the like, being executed by the computer hardware and network elements, it is not intended that any embodiments of the disclosure be limited to a particular set of computer-executable instructions or protocols.

Again, with primary reference to FIGS. 1 and 2, one or more client computing devices 3, one or more service provider computing devices 4 or patient computing devices 5 can be configured to connect with one or more server computers 2 through a wide area network ("WAN"), such as the Internet 7, or one or more cellular-based networks 8, or one or more local area networks 9 to transfer system content 12, including computer data processed or stored by a computer including, but not necessarily limited to text documents, images, audio clips, software programs, or other types of data. The one or more client computing devices 3, the one or more service provider computing devices 4 and the patient computing devices 5 can as to some embodiments take the form of one or more corresponding limited-capability computers designed specifically for navigation on the World Wide Web of the Internet 7. Alternatively, the client computing devices 3, the service provider computing devices 4, or the patient computing devices 5 might be hand-held devices such as smart phones, slate or pad computers, personal digital assistants or camera/cell phones, or multiprocessor systems, microprocessor-based or programmable consumer electronics, network PCs, minicomputers, mainframe computers, or the like.

Again, with primary reference to FIGS. 1 and 2, each of the one or more client devices 3 and the one or more service provider devices 4 and the one or more patient devices 5 can include an Internet browser 13 (also referred to as a "browser") such as Microsoft's INTERNET EXPLORER, GOOGLE CHROME, MOZILLA, FIREFOX, or the like, which functions to download and render multimedia content that is formatted in "hypertext markup language" (HTML). In this environment, a server computer 2 can include a processor 14 communicatively coupled to a non-transitory computer readable medium 15 containing 16computer program 16 may be programmed to implement the most significant portions of a graphical user interface interface(s) 17 retrievable for display on a display surface 18 based on access privileges of the corresponding client computing device 3, service provider computing device 4 or patient computing device 5 as one more client user interfaces 17A, 17B, one or more service provider interfaces 17C or one or more patient interfaces 17D. As to these embodiments, the computer program 16 which implements the one or more client user interface(s) 17A, 17B, the one or more service provider interfaces 17C, and the one or more patient user interfaces 17D can be resident in one or more server computers 2 and the one or more client devices 3, the one or more service provider devices 4, and the one or more patient devices 5 can use the browser 13 to display downloaded system content 12 and to relay user inputs 19 back to the one or more server computers 2. The one or more server computers 2 would respond by formatting new screen displays for the respective client, provider and patient user interfaces 17A, 17B, 17C, 17D and downloading them for display on the display surface 18 of the one or more client, service provider, or patient computing devices 3, 4, 5.

In other embodiments, the one or more server computers 2 can be used primarily as sources of system content 12, with primary responsibility for implementing the client, service provider, or patient user interfaces 17A, 17B, 17C 17D being placed upon each of the one or more client, service provider or patient computing devices 3, 4, 5. As to these embodiments, each of the one or more client, service provider, or patient computing devices 3, 4, 5 can contain and run the appropriate portions of the computer program 16 implementing the client, service provider, or patient user interfaces 17A, 17B, 17C, 17D, as further described below.

In some embodiments, server computer(s) 2 can include a graphical user interface application 20 which functions to store and serve the corresponding portions of the computer program 16 to the one or more client, service provide or patient computing devices 3, 4, 5 with the primary responsibility for implementing the client, service provider, and patient user interface(s) 17A, 17B, 17C, 17D being placed upon each of the one or more client, service provider, and patient computing devices 3, 4, 5. Each of the one or more client, service provider, and patient computing devices 3, 4, 5 can run the appropriate portions of the computer program 16 to implement the client, service provider and patient user interfaces 17A, 17B, 17C, 17D.

Again, with primary reference to FIGS. 1 and 2, in some embodiments, the server 2 can include an orthodontic treatment application 21 which can, include a digital converter 22 executable to digitally convert captured images 23 including images of the dental arch 24. Captured images 23 of the dental arch 24 can be achieved using a wide variety of existing and prospective optical technologies 25. As illustrative examples, digital imaging using a camera of a cell phone, computer-aided design/computer-aided manufacturing (also known as "CAD/CAM"), intraoral three-dimensional x-ray, confocal laser microscopy, active wave-front sampling, accordion fringe interferometry, optical coherent tomography, digital imaging, or combinations thereof.

Referring to FIGS. 1 and 2, digital converter 22 operates to digitally convert captured images 23 of one or both of the upper and lower dental arches 24 into virtual dental arches 26, which may, but need not necessarily, be fitted with braces, which can be depicted on the display surface 18 of one or more of the client computing devices 3, service provider computing devices 4, or the patient computing devices 5.

Again, with primary reference to FIGS. 1 and 2, the virtual dental arches 26 can include one or more views of only the upper or lower dental arch and having the occlusal surfaces engaged or disengaged including or consisting of one or more of: a labial view, an occlusal view or a lingual view, whether serially presented as discrete images, or as, a plurality of views concurrently presented, whether side by side, superimposed, in multiple discrete presentation fields, animated or looped animation from pre-treatment dental arch to post-treatment dental arch to prospective treatment dental arch, or combinations thereof. For the purposes of this disclosure the term "virtual" means a simulant of an object made by processing computer executable instructions of the orthodontic treatment application 21.

Now, with primary reference to FIG. 1, in some embodiments, the digital converter 22 or operation of the digital converter 22, can be omitted where digitized information including the virtual dental arch 26 can be accessed and retrieved for presentation on the client, service provider, or patient computing devices 3, 4, 5 without digital conversion. For example, a virtual dental arch 26 prior to or during orthodontic treatment can be retrieved over the wide area network 7, cellular-based wireless network 8, or the local area network 9 from one or more server computers 2 and the virtual dental arch 26 or any one of a plurality of virtual dental arches 26, can be depicted on the client, service provider or patient computing devices 3, 4, 5 discretely or concurrently (whether side by side, superimposed, in multiple discrete presentation fields, animated or looped animation from pre-treatment dental arch to post-treatment dental arch to prospective treatment dental arch, or combinations thereof).

A client user 27A, 27B, a service provider user 28 or a patient user 29 may enter commands and information into a corresponding one or more client 3, service provider 4 or patient computing devices 5 through input devices 30 such as a keyboard 31 or a pointing device 32 such as a mouse 33; however, any method or device that converts user action into commands and information can be utilized including, but not limited to: a microphone, joystick, game pad, touch screen, or the like. A display surface 18, such as the graphical display surface, provided by a monitor screen or other type of display device can also be connected to the client, service provider, or patient computing devices 3, 4, 5 by a display interface 34 (such as a video adapter). The client, service provider, or patient user interface 17A, 17B, 17C, 17D can in part or whole be presented as an interactive graphic interface on the display surface 18 of the client, service provider, or patient computing device 3, 4, 5. In addition, each of the one or more client, service provider or patient computing devices 3, 4, 5 can further include peripheral input devices 35 such as an image capture device 36, for example a camera, video camera, web camera, mobile phone camera, video phone, or the like, and an audio capture device 37 such as microphones, speaker phones, computer microphones, or the like. The audio capture device 37 can be provided separately from or integral with the image capture device 36. The image capture device 36 and the audio capture device 37 can be integral or connected to the client, service provider, or patient computing device 3, 4, 5 by an image capture interface 38 and an audio capture interface 39.

Now, with primary reference to FIG. 2, as a non-limiting example, the client, service provider or patient computing device 3, 4, 5 can include a processing unit 40, one or more non-transitory memory elements 41 and a bus 42 (which operably couples components of the client device 3 including without limitation the memory elements 41 to the processing unit 40. The processing unit 40 can comprise one central-processing unit (CPU), or a plurality of processing units which operate in parallel to process digital information. The bus 42 may be any of several types of bus configurations including a memory bus or memory controller, a peripheral bus, and a local bus using any of a variety of bus architectures. The memory element 41 can without limitation be a read only memory (ROM) 43 or a random-access memory (RAM) 44, or both. A basic input/output system (BIOS) 45, containing routines that assist transfer of data between the components of the client, service provider, or patient computing device 3, 4, 5, such as during start-up, can be stored in ROM 43. The client, service provider, and patient computing device 3, 4, 5 can further include one or more of a hard disk drive 46 for reading from and writing to a hard disk 47, a magnetic disk drive 48 for reading from or writing to a removable magnetic disk 49, and an optical disk drive 50 for reading from or writing to a removable optical disk 51 such as a CD ROM or other optical media, or other computer readable media. The hard disk drive 46, magnetic disk drive 48, and optical disk drive 50 can be connected to the bus 42 by a hard disk drive interface 52, a magnetic disk drive interface 53, and an optical disk drive interface 54, or other interface compatible with computer readable media, respectively. The drives and their associated computer-readable media can provide nonvolatile storage of computer-readable instructions, data structures, program modules and other data for the client, service provider, or patient computing device 3, 4 ,5. It can be appreciated by those skilled in the art that any type of computer-readable media that can store data that is accessible by a computer, such as magnetic cassettes, flash memory cards, digital video disks, Bernoulli cartridges, random access memories (RAMs), read only memories (ROMs), and the like, may be used in a variety of operating environments. A number of program applications may be stored on the hard disk drive 46, magnetic disk 49, optical disk 51, ROM 43, or RAM 44, including an operating system 55, one or a plurality of application programs 56 and without limitation the computer program 16 or the orthodontic treatment application 21 (to the extent not stored in a one or more server computers 2 which implements the client, service provider, and patient user interface(s) 17A, 17B, 17C, 17D or other program interfaces.

A "click event" occurs when the client, service provider, or patient user 27A, 27B, 28, 29 operates a function of the computer program 16 or the orthodontic treatment application 21 through the use of a command, for example, pressing or releasing the left mouse button while a pointer icon is located over a control icon (or other interactive field which activates a function) displayed in any one of the client, service provider, or patient user interfaces 17A, 17B 17C, 17D. However, it is not intended that a "click event" be limited to the press and release of the left mouse button on a mouse while a pointer is located over a control icon (or field), rather, a "click event" is intended to broadly encompass a command by a client, service provider, or patient user 27A, 27B, 28, 29 through which a function of the computer program 16, the orthodontic treatment application 21, or other application program 56 (or other program, application, module or the like) which implements the client, service provider, or patient user interface 17A, 17B, 17C, 17D or through which a function thereof can be activated or performed, whether through selection of one or a plurality of control icon(s) or fields, or by user voice command, keyboard stroke, mouse button, or otherwise.

The one or more client, service provider, and patient computing devices 3, 4, 5 can operate in a networked environment using one or more logical connections 57 to transfer user input 1919 and to connect to one or more of server computers 2. These logical connections 57 can be achieved by one or more communication devices 58 coupled to or a part of the one or more client, service provider and patient computing devices 3, 4, 5; however, the disclosure is not limited to a particular type of communications device 58. The logical connections 57 depicted in FIG. 2 can include a local-area network (LAN) 9 or a wide-area network (WAN) 7. Such networking environments are commonplace in offices, enterprise-wide computer networks, intranets, wireless networks, global satellite networks, cellular phone networks and the Internet 7.

When used in a LAN-networking environment, the client, service provider, or patient computing device 3, 4, 5 can be connected to the local area network through a network interface 59, which is one type of communications device 58. When used in a WAN-networking environment, the client, service provider and the patient computing device 3, 4, 5 typically include a network interface 59 (e.g., a modem), a type of communications device 58, or any other type of communications device for establishing communications over the wide area network 7, such as the Internet. Network interface 59, which may be internal or external, can be connected to the bus 42 via a serial port interface 60. In a networked environment, the computer program 16 or the orthodontic treatment application 21 depicted relative to the client, service provider, or patient computing device 3, 4, 5, or portions thereof, may be stored in the one or more server computers 2, as above described. It is appreciated that the network connections shown are exemplary and other means of and communications devices for establishing a communications link between the client, service provider, and patient computing devices 3, 4, 5 and the one or more server computers 2 can be used.

Figure 3:
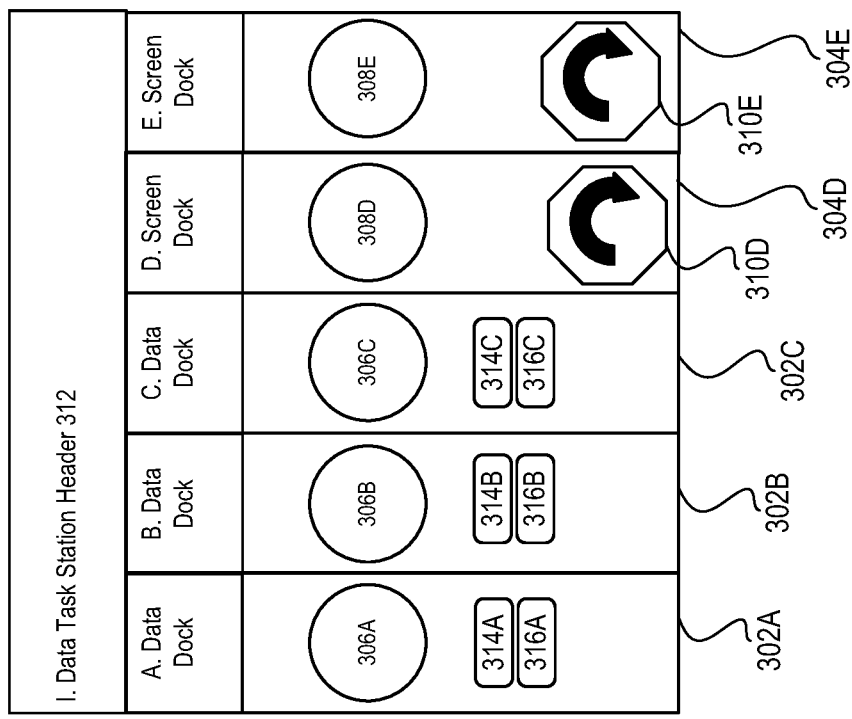
FIG. 3 is a block diagram illustrating an exemplary data task station, according to example embodiments.

FIG. 3 is a block diagram illustrating a generic data processing station 300, according to example embodiments. In some embodiments, server 2 may include computer program 16. Computer program 16 may be configured to enable a plurality of data task stations, such as data task station 300 and the various data task stations described below in conjunction with FIGS. 4A-4E.

Data task station 300 may be accessible via one or more of a client device 3, service provider 4, and/or patient computing device 5. In some embodiments, data task station 300 may only be accessible to a subset of client device 3, service provider 4, or patient computing device 5. By limiting the accessibility of data task station 300, server 2 may protect any sensitive information, as well as reducing the amount of data to be reviewed by each respective party. In this manner, data task station 300 may be configured in a manner, such that only specified parties may gain access to a respective data task station 300. Within the system 1 there may be an infinite number of data task stations 300.

In some embodiments, computer program 16 may selectively enable and/or disable data task station 300 and/or content receiver 90. When a data task station 300 and associated content receiver 90 are each enabled, data task station 300 can accept and transfer data content to data content receiver 90. In some embodiments, when a data task station 300 and content receiver 90 are enabled, data content can simultaneously reside in content receiver 90 and a respective data dock of the enabled data task station 300.

A series of data task stations 300, may be connected within the system 1. As shown, data task station 300 may include at least one data dock 302 and at least one screen dock 304. For example, data task station 300 may include data dock 302A, data dock 302B, and data dock 302C (generally, "data dock 302"). Data task station 300 may further include screen dock 304D and screen dock 304E (generally, "screen dock 304"). Although FIG. 3 provides three data docks 302 and two screen docks 304, those skilled in the art recognize that data task station 300 may include a greater or fewer number of data docks 302 and/or screen docks 304.

In some embodiments, data content receiver 90 may act as an aggregator within a data task station 300 and/or across data task stations 300. For example, data content receiver 90 may be configured to receive and compile all data content entered into the various data docks 302 to form a data record. In some embodiments, the data record may be maintained at a respective data dock 302 or, more broadly, a data task station 300. In some embodiments, the data record may reside in data content receiver 90. For example, when data is entered in data dock 302A, 16 computer program 16 may be configured to generate a data record (e.g., a patient card) of the data input to data dock 302. In some embodiments, the data record may be associated with a client, customer, user, or patient.

Data dock 302 may be configured to receive, display, and request a data record be moved within data task station 300 and between numerous data task stations 300. Each data dock 302 may include a respective data portal 306. For example, data dock 302A may include data portal 306A, data dock 302B may include data portal 306B, and data dock 302C may include data portal 306C. Data portal 306 may be configured to receive the requisite information prompted by the respective data dock. For example, a user can provide data through a data portal 306 to satisfy or begin to satisfy predetermined data content requirements associated with a respective data dock 302. In some embodiments, each data portal 306 may be in communication with one or more data content receivers 90. For example, data content entered into a respective data dock 302 may be passed through a respective data portal 306, and from data portal 306 to a data content receiver 90. Data content passed to data content receiver 90 may be considered associated with data content receiver 90. Data may be able to simultaneously reside in data dock 302 and an associated data content receiver 90.

In some embodiments, each data dock 302 may be associated with an activator 314. An activator 314 may activate data portal 306 to receive specific data content. In operation, a user can provide data through a respective data portal 306 to satisfy or begin to satisfy predetermined data content requirement associated with a respective data dock 302 following activation by activator 314. Data content receiver 90 may receive this data, via data portal 306, and associate this data with a particular data record within a respective data dock 302. Each data dock 302 may receive data from a data receiver 90 or from the data intake of its associated data task station 300, or from one or more of client device 3, service provider device 4, and/or patient computing device 5. In some embodiments, the data can be received at a data task station 300 with or without the data receiver 90. As provided above, computer program 16 may further be configured to screen data content associated with a data content receiver against a pre-determined data content requirement of a data task station. In some embodiments, the predetermined data requirement can be all the data required by a particular data task station 300, data dock 302, and/or screen dock 304. For example, the predetermined data content requirement can refer to the data against which data content is screened.

In some embodiments, each data dock 302 may be associated with an aggregator 316. Aggregator 316 may be configured to identify data relevant to a data dock 302 and add that data to a corresponding data record in a data dock 302. Each screen dock 304 may be configured to receive data from data receiver 90 and/or directly from a user. For example, screen dock 304 may be configured to receive a data record associated with a user from a data dock 302. In some embodiments, screen dock 304 may receive data from data dock 302 responsive to a user dragging and dropping the patient card from a data dock 302 into screen dock 304. Those skilled in the art understand that moving data between data docks 302 or between data docks 302 and screen dock 304 may be done through various inputs and is not limited to the dragging and dropping of a graphical element (e.g., tile or card) among data docks 302 and screen docks 304.

Each screen dock 304 may include a screen portal 308. Screen portal 308 may be configured to screen data that may be input to screen dock 304. For example, upon receiving data (e.g., a tile or a card) from a data dock 302, screen portal 308 may be configured to analyze the data contained therein to determine whether the requisite information has been provided. To screen data provided to screen dock 304, screen portal 308 may compare the data against pre-determined data content requirements of a data task station 300 or, more granularly, a data dock 302. If screen portal 308 determines that the data content requirements of a data task station 300 or data dock 302 are not met, then screen portal 308 may reject the data input. For example, screen portal 308 may send the data back to an origination data dock 302 for the required information. If, however, screen portal 308 determines that the data content requirements have been met, then screen portal 308 may continue processing the data.

As shown, each screen dock 304 may further include an automator 310. Automator 310 may be configured to perform one or more data automations. For example, upon screen portal 308 determining that the data content requirements have been met for data input to screen dock 304, screen portal 308 may provide the data to automator 310. Automator 310 may include executable code to pass the data record from data task station 300 to a different data task station, as described in more detail below. Other automations may include but are not limited to modifying the data record by creating or modifying a due date, creating or modifying a descriptive tag, creating or modifying an assignee, and the like. Additionally, an automator 310 may contain executable code to pass the data record from a data task station 300 to an external system. This may also include sending an external notification such as an email or text communication.

The data record may be movable among data docks 302 and/or screen docks 304. For example, data record may be embodied as a graphical tile or card associated with a user that may be moved from data dock 302A to screen dock 304. As the data record is passed among data docks 302 and/or screen docks 304, computer code may continually aggregate the user data. For example, as the data record is passed among data docks 302, the computer code may continuously build update the data record for a good, product service, customer, client, and/or patient by adding information to the data record. In this manner, any authorized end user may access the data record in data task station 300 to view information within a data record.

The data input at each data dock 302 may determine where the data record may be transferred by an automator 310. In some embodiments, there is no one direct path a given data record may take. Every data record is unique; as such, real time circumstances related to a particular data record may determine the path the data record may take. Every data dock 302 may present a unique data request. For example, the action automator 310 may take may be determined using on the most recent data input. Similar to playing chess, even though all of the known paths a data record may take have been predetermined, which particular path the data record does take is independently determined by the input received at each data dock. This makes the overall path a data record may take completely unpredictable. This is an example of how multi-criteria decision making is employed in structured controlled manner. Each decision may alter the variables involved in making successive decisions.

In some embodiments, data task station 300 may include a header 312. Header 312 may uniquely identify data task station 300. Header 312 may be related to the subject matter of the content associated with a given data task station 300. For example, each data dock 302 of a given data task station 300 may be configured to receive, display, and/or request information related to a similar topic, such as, but not limited to, marketing.

Data passing within and between data task stations, data received by a data content receiver which may be associated with a data task station 300, as well as any data transferred to an external system from within the system 1, may be encrypted prior to transfer. Embodiments may include SSL/TLS encryption methods, API authentication methods such as password, multi-factor authentication, and/or an authentication token, encryption at rest and in transit, database may be encrypted upon API query, and/or an encrypted VPN tunnel. In some embodiments, personal identifiers may be replaced by a unique identifier as additional security. In some embodiments software as a service may be employed for additional security.

Each data task station 300 may have one or a set of authorized users. Authorized users with access to a given data task station may have training, skill, and knowledge related to subject matter which may be identified by a header 312 associated with a given data task station 300. For example, all authorized users with access to the data task station 300 cited in the previous two examples, may have training, skill, and knowledge in marketing.

In some embodiments authorized users may have various levels of permission to access one or more data task stations 300 or one or more data docks 302. Examples of permissions may include, but are not limited to, access to view but not modify a record, access to view predetermined data task station, access to view predetermined data docks, access to view and modify a record, access to view and modify records visible at predetermined data task stations, and/or access to view and modify records visible at predetermined data docks.

Each data dock 302 may be configured to display all or only a portion of the data received. For example, each data dock 302 may be configured to display only the content relevant to an authorized user.

Each data dock 302 may be configured to display a request and/or receive specific information from an authorized user. For example, each data dock 302 may include one or more fields that prompt a user to enter requisite information. In some embodiments, each data dock 302 may display unique data fields or a unique set of data fields. In some embodiments, data fields for a first data dock (e.g., data dock 302A) can overlap with data fields of another data dock (e.g., data dock 302B). Each data field displayed in each data dock 302 may be configured to receive only the data content required for that data dock.

Examples of a data request the computer code may display to an authorized user may include, but are not limited to a checklist of items, one or more data fields, upload of a specific file type, open ended questions, and the like. In this manner, an authorized user may view real time operating information when a data record is accessed. Delivery of real time operating information to an authorized user improves efficiencies, allows for optimal allocation of resources, and decreases errors.

In some embodiments the data records shown in the data docks may be sorted based on due date, authorized user assigned to a data record, type of content within the data record, and the like.

In some embodiments data task stations may have limits set to not allow data records to populate or have a due date within a certain time frame. This may allow for a "vacation mode." This also may be set to prevent tasks due dates from falling on weekends.

In some embodiments the administrator may have the option to only view data records due that day or within a set number of days. Once the tasks required in each data record have been completed by the administrator, the data dock may not show any additional data records. Any data records which may have a due date outside the selected time frame may not be visible to the administrator with access to that data task station.

In some embodiments, each data dock 302 may be configured to transfer the information entered into data fields to an external system. As an example, a set of data fields which receive information input from a user may with access to a data dock 302 may have one or more integrations enabled using one or more application programming interfaces (APIs) or a health level 7 integration, which link functionality of one or more external systems to a data dock 302. This integration may enable the information entered into data fields at a data dock 302 to be compiled and sent outside the system via a text communication, email, notification, and the like.

In some embodiments, data task stations 300 may support integration with one or more management systems. For example, a health level 7 integration may exist between the two. Data task station 300 may support the facilitation of data to an external or internal management. Exemplary sets of information may include prescription information, physical patient records, communication between employee of office and patient or user, changes in status of lab orders, and various notifications. In some embodiments, data task station 300 may support an integration with a shipping service for tracking and arrival notification. Additionally, in some embodiments a product, good, or medical device may have a quick response code on the packaging. This code may be scanned by the recipient, which may have an integration with an activator 314. This activator 314 may be associated with data dock 302 or screen dock 304, which may activate a data content receiver 90 to receive data. Such data may include recipient, date, time, and/or location of delivery.

In some embodiments, each data dock 302 may include one or more integrations associated therewith. The one or more integrations may allow a data task station 300 to communicate with one or more external systems. In some embodiments, the one or more integrations may be enabled using one or more application programming interfaces (APIs) that link functionality of the one or more external systems to data task station 300. In this manner, a user may navigate away from a data task station 300 to a third-party website or web page directly from a data dock 302. A third-party website or web page which may be accessed via a data dock 302 may contain information needed for review by an authorize user. An authorized user may review this information and input the data requested by a data dock 302.

In some embodiments, rather than navigating the user away from data task station 300, server 2 may generate a portal within computer program 16, such that the user remains within computer program 16. In other words, server 2 may be configured to render a third-party website within the native computer program 16 environment.

In some embodiments, an action taken by a user authorized to access a data dock 302 may be relayed to an external system. For example, an authorized user may click an action button within native computer program 16, which may cause computer code to relay this action via server 2 to a third-party website. Using a more specific example, an authorized user may be able to approve an order from a third-party vendor via an action button rendered within a data dock 302.

Data task station 300 may support one or more integrations and automations. For example, data task station 300 may integrate a web-based provider locator. The provider locator may have a linked scheduler (e.g., Acuity). This may integrate via an API or HL7 integration and populate demographic and appointment information within a data task station 300. In some embodiments, data task station 300 may support automated marketing to lead until they schedule. In some embodiments, data task station 300 may automate reminders until intake paperwork is completed after scheduling.

In some embodiments, data task station 300 may support import and viewing of insurance information once submitted by via an online portal. In some embodiments, data task station 300 may support automated reminders for appointment. In some embodiments, such as those involving collection of an intra-oral scan at evaluation, the scanner may integrate with the server 2 and/or a doctor site (e.g., Invisalign Doctor Site (IDS)) to automatically create and populate required composite of images. In some embodiments, after taking intra-oral scan on patient, form fields to complete aligner prescription which may be populated into a data dock 302 of a data task station 300. In some embodiments, a data record may include a button or link that allows an authorized user to view intra-oral scan, composites, prescriptions, etc. associated with a patient.

In some embodiments, data task station 300 may support extra-oral photos. For example, extra-oral photos may be captured by a camera on scanner and integrated into a data dock. In another example, extra-oral photos and scanner images may be compiled to create a composite. In another example, extra-oral photos may be added wirelessly or through scanner website to complete composite. In some embodiments, a patient's email may be entered into a scanner to email composite photos and predicted outcome to patient.

In some embodiments, the system may support automated emails. For example, the present system may send an automated email after contract is signed. It may include a predicted treatment or service outcome.

In some embodiments, the system may support various integrations with various third-party financing platforms. Data may populate within a data dock when an application is filled out, approved, declined, funds provided, and the like.

In some embodiments, the present system may include a data dock integration for an automated method for submitting a prescription to lab once third-party financing approved. An automated SMS/email may be sent to patient with link to schedule appointment.

In some embodiments, the system may support various integrations with an IDS. For example, various IDS integrations may include, but are not limited to, a prescription submission, a records submission, a visualization system (e.g., Invsalign Clinchek), a number of days waiting after each modification, an updated due date for each modification, a notification for when aligners are manufactured, a notification for when aligners are shipped, a QR code scanning when aligners arrive in office, and the like.

In some embodiments, the system may include prepopulated prescription options within a drop-down menu at a data dock 302., Automated renewal or subscriptions for appliances may be included as data records are moved within and between data task stations. SMS, text message, email, etc. sent to a patient at predetermined intervals with payment option, and the like.

In some embodiments, the system may support the ordering of appliances or other items from a data dock. For example, the system may include a form that populates with drop down to submit for additional appliances with prescription, drop down option to send patient message for in office appointment needed. Additional appliance submission may be submitted from new scan or option to automate from a prior stage In some embodiments, a screen dock may send an email or SMS offering a service or treatment upgrade.

In some embodiments, a data dock may support templated responses and videos sent at predetermined intervals, such as instruction video, emergency video, appliance seating video, and the like.

Such functionality provides an improvement on current multi-criteria decision making techniques within organizations. In some embodiments this computer implemented system has advantages by receiving, screening, aggregating, and transferring real time information sequentially within and between data task stations 300.

Figure 4A:
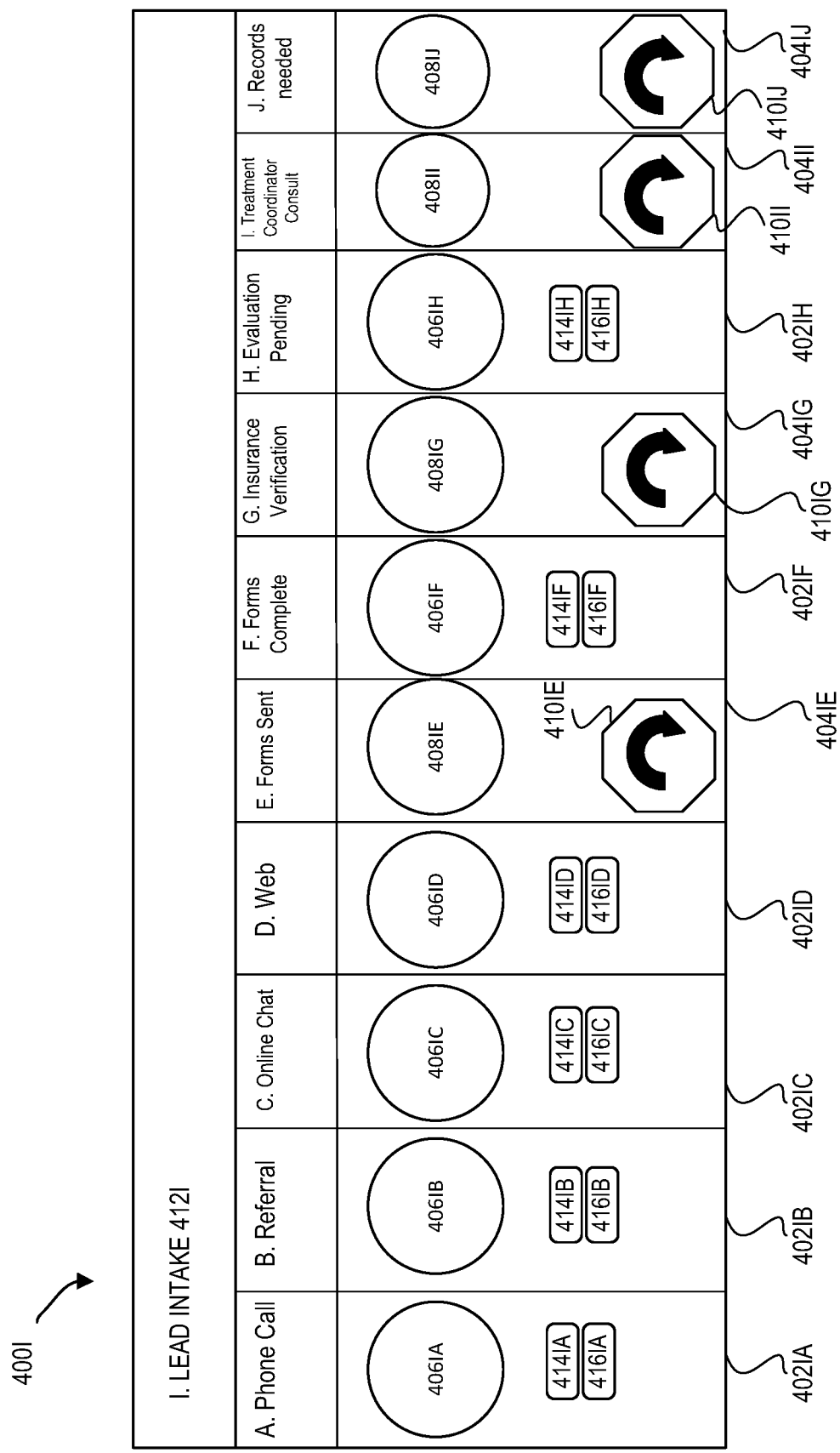
FIG. 4A illustrates an exemplary data task station, according to example embodiments.
Figure 4C:
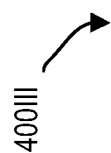
FIG. 4C illustrates an exemplary data task station, according to example embodiments.

FIG. 4A is a block diagram illustrating a first data task station 400I ("I. LEAD INTAKE"), according to example embodiments. FIGS. 4B1 and 4B2 are block diagrams illustrating a second data task station 400II ("II. FINANCIAL"), according to example embodiments. FIG. 4C is a block diagram illustrating a third data task station 400III ("III. RECORDS"), according to example embodiments. FIGS. 4D1 and D2 are block diagrams illustrating a fourth data task station 400IV ("IV. PROVIDER REVIEW"), according to example embodiments. FIGS. 4E1 and E2 are block diagrams illustrating a fifth data task station 400V ("V. VIRTUAL MONITORING"), according to example embodiments. Each of data task station 400I-400V may be representative of exemplary data task stations based on data task station 300 discussed above in conjunction with FIG. 3. Data task stations 400I-400V may be part of a healthcare system that provides each party to the healthcare process with the requisite information needed to complete each part of a healthcare workflow. Those skilled in the art recognize that data task stations 400I-400III are not limiting and that additional data docks, screen docks, or data task stations may be added to the overall workflow, depending on the needs of the end users.

For ease of discussion, a data task station generally may be referred to as "data task station 400," a data dock generally may be referred to as "data dock 402," a screen dock generally may be referred to as "screen dock 404," a data portal generally may be referred to as "data portal 406," a screen portal generally may be referred to as "screen portal 408," an automator generally may be referred to as "automator 410," a header generally may be referred to as "header 412," and an activator may generally be referred to as "activator 414." When a specific instance of any of the aforementioned elements is recited, it may be followed by a corresponding data task station number, data dock number, and/or screen dock number. As an example, in FIG. 4A, data task station 400, may be data task station 400I. A data dock displayed with data task station 400I may be data dock 402I.

As shown, data task station 400I may correspond to a first data task station titled: "I. LEAD INTAKE." Data task station 400I may include a plurality of data docks 402I. For example, data task station 400I may include data dock 402IA ("A. PHONE CALL"), data dock 402IB ("B. REFERRAL"), data dock 402IC ("C. ONLINE CHAT"), data dock 402ID ("D. WEB"), data dock 402IF ("F. FORMS COMPLETE"), and data dock 402IH ("H. EVALUATION PENDING"). Data task station 400I may further include a plurality of screen docks 404I. For example, data task station 400I may include screen dock 404IE ("E. FORMS SENT"), screen dock 404IG ("G. INSURANCE VERIFICATION"), screen dock 404II ("I. TREATMENT COORDINATOR CONSULTATION"), and screen dock 404IJ ("J. RECORDS NEEDED"). As provided, data task station 400I may receive initial data content 72 from one or more of client device 3, service provider device 4, and/or patient computing device 5.

Data task station 400II may correspond to a second data task station titled "II. FINANCIAL." Data task station 400II may include a plurality of data docks 402II. For example, data task station 400II may include data dock 402IIA ("A. NEED VERIFICATION"), data dock 402IID ("D. CONTRACT RECEIVED"), data dock 402IIG ("G. FILE CLAIM"), data dock 402IIH ("H. CLAIM FILED"), data dock 402III ("I. FROM INSURANCE"), data dock 402IIJ ("J. PAYMENT RECEIVED"), data dock 402IIK ("K. EXPLANATION OF BENEFITS"), data dock 402IIL ("L. CONTRACT ADJUSTED"), data dock 402IIO ("0. REVIEWED"), and data dock 402IIP ("P. DECLINED"). Data task station 400II may further include a plurality of screen docks 404II. For example, data task station 400I may include screen dock 404IIB ("B. VERIFIED"), screen dock 404IIC ("C. CONTRACT SENT"), screen dock 404IIE ("E. READY FOR SUBMISSION"), screen dock 404IIF ("F. UPDATE RECORDS"), screen dock 404IIM ("M. COMPLETE"), screen dock 404IIN ("N. NEEDS REVIEW"), and screen dock 404IIQ ("Q. RESOLVED"). As provided, data task station 400II may receive data content from one or more of client device 3, service provider device 4, and/or patient computing device 5. In some embodiments, data task station 400II may automatically receive data content via content receiver 90.

Data task station 400III may include data dock 402IIIA ("A. SCHEDULED") and data dock 402IIIB ("B. ALL SCANS"). Data task station 400III may further include screen dock 404IIIC ("C. EVALUATION"), screen dock 404IIID ("D. TREATMENT COORDINATOR CONSULTATION"), screen dock 404IIIE ("E. RETAINERS"), screen dock 404IIIF ("F. GROWTH AND GUIDANCE"), screen dock 404IIIG ("G. APPLIANCE"), screen dock 404IIIH ("G. ACTIVE SUBMISSION"), screen dock 404IIII ("I. PROGRESS REVIEW"), and screen dock 404IIIJ ("J. FINALS").

Data task station 400IV may include data dock 402IVA ("A. VIRTUAL VISITS"), data dock 402IVC ("C. CONSULT AND GROWTH AND GUIDANCE"), data dock 402IVE ("E. CLINICAL"), data dock 402IVG ("G. LAB"), data dock 402IVK ("K. FINANCIAL"), and data dock 402IVM ("M. FINAL"). Data task station 400IV may further include screen dock 404IVB ("B. REVIEWED"), screen dock 404IVD ("D. REVIEWED"), screen dock 404IVF ("F. REVIEWED"), screen dock 404IVH ("H. ALIGNERS"), screen dock 404IVI ("I. INDIRECT BONDING"), screen dock 404IVJ ("G. IN-HOUSE"), screen dock 404IVL ("L. REVIEWED"), and screen dock 404IVN ("N. REVIEWED").

FIG. 4E1 and FIG. 4E2 are a block diagrams illustrating data task station 400V ("V. VIRTUAL MONITORING"), according to example embodiments. Data task station 400V is shown across two separate sheets for ease of discussion. As shown, data task station 400V may include data dock 402VA ("A. SCHEDULED"), data dock 402VD ("D. INCOMING"), data dock 402VE ("E. RETAINERS"), data dock 402VF ("F. ALIGNERS"), data dock 402VG ("E. IN-HOUSE"), data dock 402VH ("H. APPLIANCE"), data dock 402VI ("I. ELASTICS"), data dock 402VK ("K. REVIEWED"), data dock 402VL ("L. COMMUNICATION SENT"), and data dock 402VM ("M. NEED RECORDS"). Data task station 400V may further include screen dock 404VB ("B. FIRST SENT"), screen dock 404VC ("C. SECOND SENT"), screen dock 404VJ ("J. PROVIDER REVIEW"), screen dock 404VN ("N. NEXT VIRTUAL VISIT"), screen dock 404VO ("O. MANUFACTURE NEXT"), and screen dock 404VP ("P. SUBSCRIPTION PROGRAM"). In some embodiments, data task station 400V may act as a virtual visit board. For example, data task station 400V may provide a form (e.g., in data dock 402VA) that populates with drop down to submit for additional aligners with prescription, a drop-down option to send patient message for in office appointment, if needed, and the like.

As those skilled in the art know, the process of onboarding a new client, customer, and/or patient requires multi-criteria decision making. In some embodiments, computer program 16 may function via data portals 406, screen portals 408, automators 410, and/or activators 414 to receive, display, request, modify, and/or transfer data in an appropriate controlled order.

In some embodiments, data task station 400I may be associated with receiving leads from external sources. These leads may represent a potential client, customer, or patient. As those skilled in the art understand, an organization may receive leads from a plethora of external sources. Data docks 402 within this data task station 400I, may be associated with different sources which may receive information about a lead. An example list of sources includes but is not limited to, phone call, referral, online chat, web inquiry, a provider locator service and the like. External data may be received at one or more data docks 402I. Each data dock 402I, may be configured to receive data from a different source. A data dock 402I which may be configured to receive a lead may have an activator 414 associated. An activator 414 specific to a data dock 402I may activate data content receiver 90 to receive data from a specific external source.

Each data dock 402I, may also be configured to display all or a portion of the content received. A data dock 402I may also be configured to display a unique data request to an authorized user based on the initial data content received. For example, data dock 402IA may display a set of data fields to an authorized user, this set of data fields may be completely unique or have some overlap with data fields displayed to a user by data dock 402IB.

An authorized user may be prompted to complete these data fields. In some embodiments once this information is received by a data dock 402, a copy of the data may be transferred to an external system. As an example, in some embodiments, information received by a data dock 402 may be transferred to an office management software.

In some embodiments, examples of requested data may include but are not limited to basic contact information, insurance information, service or goods requested, payment information, request for file and/or document to be uploaded, ordering information, laboratory prescription or orders, a checklist and the like. The request may be represented as drop down selection, open ended question format, attachment upload and the like.

In some embodiments, data docks 402IB-D may be configured to receive data from an external source. Each data dock 402 may be configured to receive a unique data set. For example, data dock 402IB. Referral may be configured to receive data containing contact information along with some type of historical data. As a specific example, a referral from one healthcare provider to another may contain healthcare records such as treatment notes, health history, diagnostic testing, and the like. A different data dock 402 such as data dock 402IC may be configured to receive basic contact information only. Whereas a data dock 402, such as data dock 402ID. Web may be configured to receive contact information, appointment date and time, along with a complete intake questionnaire.

A user may navigate to a website or web page affiliated with an office, product, good, service and/or care. The website or web page may prompt a user to input data responsive to a scheduler application within the website or web page. For example, a user may navigate to the website of a service or healthcare provider. The user may schedule an appointment via a scheduler application, (e.g., Acuity). A user may also have the option to submit an appointment inquiry via a Tillable form native to a website or web page. The data captured by the website or web page may be provided to servers 2 where an activator 414 may activate initial data content receiver 90 to receive content. The content may be received and displayed at a data dock 402 (e.g., data dock 402ID). For example, if a potential client or patient navigates to the website of a service or healthcare provider and utilizes a scheduler application within the website, servers 2 may cause the activator 414 to activate data content receiver 90 to create initial data content corresponding to the appointment. In some embodiments, server 2 may utilize a bounce back email system. For example, a bounce back email may include but is not limited to 1 a link for the user to fill out intake forms; 2 a link for the user to submit photos to review needs or qualifications for service; 3 a link for the user to view predicted outcomes of requested services (e.g., a smile outcome); and/or 4 a link to a view and/or apply for financial support from a third-party financing service.

In some embodiments, initial data content received at data dock 402ID may have already had an intake questionnaire sent. For example, a user receives intake forms via a bounce back email system after scheduling an appointment. As those skilled in the art recognize, if intake forms have already been sent, a data record would not need to be transferred to screen dock 404IE. This may allow the data record to bypass screen dock, 404IE. However, an authorized user may review a data record visible at data dock 402D, and mistakenly move this data record to screen dock 404IE. The data within the data record may be screened against a predetermined data content requirement. If screen portal 408, such as screen portal 408IE, determines that the data content requirements of data dock 402IE are not met, then screen portal 408 may reject the data input. This prevents an authorized user from moving a data record down the wrong path.

In some embodiments, initial data content received at data docks 402IA-C, may not contain a complete intake questionnaire. Data records from 402IA-C may be passed to screen dock 404IE in order to collect the necessary data. If a data record displayed at data docks 402IA-C is not transferred to screen dock 404IE by an authorized user, it may not pass a screen against a predetermined data requirement at any other screen dock 404. This prevents a data record from progressing before collecting all required information.

A data record moved from data docks 402IA-C by an authorized user to screen dock 404IE may be screened by a screen portal 408IE. A screen portal 408IE may screen the data content against a predetermined data requirement. If the requirement is met, the screen is passed and an automator 410IE may be activated. This automator may perform one or more automations. In some embodiments, automator 410IE may send an intake questionnaire to a party specified within a data record. In some embodiments, screen dock 402IE may include one or more integrations with a cloud-based form automation solution such as, but not limited to JotForm commercially available from JotFrom, Inc. Automator 410IE may integrate with a cloud-based form automation software to send an intake questionnaire via email and/or text communication.

Once a user completes the intake questionnaire a submit function may be employed. An activator 414, such as activator 414IG, may activate data content receiver 90 to receive the data. Data content receiver 90 may create initial data content in data dock 402IG.

In some embodiments, a data record displayed at data dock 402ID and a data record displayed at data dock 402IG may both contain requisite data for screen dock 404IG. Despite passing through different data docks 402 and screen docks 404, before being screened at screen dock 404IG, a data record transferred from either data dock 402ID or data dock 402IG may contain the data required to pass screening. Thus, one example of how data records may take different pathways within the system, in order to collect the data needed to meet predetermined data requirements.

In some embodiments, screen dock 404IG may include a screen portal 408IG that screens the data in the data record against a predetermined data requirement for screen dock 404IG. Upon determining that the predetermined data requirement is met, automator 410IG of screen dock 404IG may perform one or more automations. For example, automator 410IG, may transfer data within a data record to a different data dock 402 or data task station 400. As a specific example, automator 410IG may transfer data within a data record to data task station 400II. Within data task station 400II, automator 410IG may transfer the data record to be displayed at data dock 402IA.

An automator 410 such, as automator 410IG, may also modify the data content. In some embodiments, automator 410IG may add a due date to a data record. In some embodiments this due date may be any date before the scheduled appointment date. As a specific example, a due date of 1 day before a scheduled appointment may be generated by an automator such as automator 410IG. In practice, this alerts an authorized user with access to a data record as to the due date for requested to be collected and added.

In some embodiments, each data task station 400 may include a header which communicates the subject matter of the data received, displayed, requested, screened, modified, and/or transferred within the data docks 402 and screen docks 404 displayed. In some embodiments, data task station 400II has the header 412 of Financials. Data docks 402 and screen docks 404 may be configured for data related to financial matters. In turn, authorized users for data task station 400II may have training, skill, and access to the information required to review and input financial data. The transferring of a data record from data task station 400I to data task station 400II by an automator 410 In some embodiments, illustrates how data may flow between subject matter experts. The present disclosure describes a way to aggregate information while passing between teams, departments, facilities, organizations, and the like. The data is only visible to a team, department, facility, organization and the like when information specific to the aforementioned is requested.

In some embodiments, a data record visible within a data dock 402 may display all or a portion of aggregated data collected at previous data docks 402. Each data dock 402 may be configured to display a request for a unique data set. In some embodiments, a data record transferred from data task station 400I, by an automator associated with screen dock 404IG may be transferred to data dock 402IIA. Data dock 402IIA may be configured to display a request for insurance eligibility and coverage for the party specified within the data record. In some embodiments, data dock 402IIA may also be configured to display the relevant data content an authorized user may need to collect and submit the requested information.

Such discussion illustrates how data task stations 400 collect and request information in a sequential rather than simultaneous manner. Each data dock 402 may display and request information needed before successive data may be added. Each authorized user is shown necessary data. Multiple authorized users are not concurrently searching for and trying to obtain the same data. For example, after an authorized user with training, skill, and access to acquire insurance coverage and eligibility adds this requested information to a data record, the data record may be transferred to screen dock 404IIB by an authorized user.

Screen dock 404IIB may include a screen portal 408IIB that screens the data in the data record against a predetermined data requirement for screen dock 404IIB. Upon determining that the predetermined data requirement is met, automator 410IIB of screen dock 404IIB may perform one or more automations. In some embodiments, automator 410IIB may move a data record to a different data task station 400. For example, automator 410IIB may move a data record to data task station 400I where the data record may be visible at data dock 402IH. Additionally, automator 410IIB may modify the data content within the data record. As an example, a due date may be added which correlates with an appointment date scheduled with the party specified within the data record.

A data record visible at data dock 402IH may include a complete intake questionnaire, insurance eligibility and coverage, and appointment date and time. This data record may have a due date associated, which may be related to the date of the scheduled appointment.

If, for example, the party specified within a data record displayed at data dock 402IH arrives for an in person scheduled appointment, an authorized user may move the data record to screen dock 404IJ. If, for example, the party specified within a data record displayed at data dock 402IH connects virtually with an office for a scheduled appointment, an authorized user may move the data record to screen docks 404IIIC of data task station 400III.

If, for example, the specified party within a data record does not keep the scheduled appointment, the due date on the data record may expire. This notifies authorized users to contact the party to reschedule. The data record may remain visible at this data dock with an expired due date until a new appointment is scheduled, or the specified party declines to reschedule. This is one example of how a data record in need of attention remains visible to authorized users with the training, skill, and ability to collect and input the needed data. An authorized user with a specific skill set does not need to seek out data records in need of said skill set.

For ease of discussion, when discussing the actions of an automator 410, it is understood that the data record has been screened by a screen portal 408 against a predetermined data requirement, and the data requirement has been met before the automator may be activated. With this being said, screen dock 404IJ may contain an automator which may transfer a data record to a different data task station 400. In some embodiments, automator 410IJ may transfer a data record to data task station 400III. In some embodiments, data task station 400III may be accessed by authorized users with training, skill, and access to equipment needed to obtain records.

For example, a data record visible at data task station 400III may have collected an intake questionnaire along with insurance coverage and eligibility information. The data may have been collected by an intake specialist and an insurance specialist respectively. The information within the intake questionnaire may screen for the necessity of an in-person appointment. An intake questionnaire may also screen for the need to obtain records. Insurance coverage and eligibility information may factor into the appropriateness of the timing or need for an in-person appointment. If this information had been collected simultaneously, by different teams, administrators, departments, etc., an in-person appointment may occur where the party specified within a data record does not exhibit a need for a product, good, service, or care provided. It may be realized at an in-person appointment that insurance coverage is not valid for the requested product, good, service, or care. If the information is collected in an appropriate order, and decisions are made based on up-to-date requisite information, mistakes such as those just described may be avoided.

In some embodiments, a data record may cycle within and between one or more data task stations 400 for an indefinite amount of time. The data record may continue repeating the same pattern of data docks 402 and screen docks 404, until a data requirement is met which triggers and automator to transfer a data record to a different data dock 402 or screen dock 404. For example, a patient may submit virtual records every month for an entire year before a healthcare provider inputs data signaling an in-office visit is needed. Once this data is received, it changes the path of a data record.

In some embodiments, the system may include a data task station associated with Virtual Monitoring. For example, the Virtual Monitoring data task station may include a plurality of data docks and a plurality of screen docks involved with receiving, displaying, and requesting information involved in a virtual monitoring process. As an example, a service or healthcare provider may have a need to follow progress of a service or treatment. It may not always be necessary to conduct a progress assessment in person. A customer, client, and/or patient may submit data which may be sufficient to monitor progress. In the example embodiment, the above data docks may all be configured to receive, display, and/or request such data.

For example, Virtual Monitoring data task station may be configured to receive input concerning a good, product, service, client, customer, and/or patient. Often, progress may be assessed remotely, before an in-person review may be needed. To this extent, in some embodiments, a data record may need to cycle within and between one or more data task stations multiple times. As a specific example, a service or treatment may require a monthly progress review. This review may occur asynchronously and may only require a text exchange or an exchange of photographs to monitor progress. In some embodiments, the Virtual Monitoring data tasks station may receive, display, request, modify, and/or transfer data related to a healthcare service.

The connectivity within and between the Virtual Monitoring data task station, external sources, and other data task stations within the system offer an improvement on current methods. For example, the Virtual Monitoring data task station may facilitate remote treatment monitoring. Activators, which may be associated with one or more data docks of the Virtual Monitoring data task station may initiate data content receiver 90 to receive data form an external source. For example, the external source may be a web page with photo submission embedded. A user may submit the requested photos. This may generate an email containing the photos. This email may have an integration, such as an API integration, with an activator associated with a given data 402. This activator may activate data content receiver 90 to receive the user photos and generate a tile or card visible at a data dock. The data dock may be configured to receive virtual monitoring data from an external source, additionally it may be configured to display a checklist to an authorized user. This checklist may outline all items needed for a healthcare provider to accurately review a data record. A data dock may also be configured to add a descriptive tag to a data record, for example virtual.

In some embodiments, an aggregator 416 may be associated with data dock 402VB. An identifier unique to the party specified within the received data content, may match a data record already within the system 1. An aggregator 416, may recognize the identifier and add the data content received with the matching data record. For example, the incoming photos may be aggregated with a data record already within the system 1. Specifically, incoming virtual records may be added to a matching data record which may be located at a data dock such as data dock 402VC or data dock 402VC Second Sent.

In some embodiments, a data record from screen dock 404VB or screen dock 404VC may now be reviewed, added to, and/or transferred by an authorized user. The data record generated at data dock 402VD Incoming may be archived. This data record may be archived because an aggregator 416, enabled by the computer program 16, may have transferred the received data to an affiliated data record at screen dock 404VB or screen dock 402VC by matching a unique identifier found in both data records.

An authorized user may review the photos and data associated with the data card. If progress cannot be assessed due to information not captured accurately in photos, an authorized user may input that additional information is needed. An authorized user may move a data record displayed at a screen dock 404, such as screen dock 404VB or screen dock 404VC to a different dock 402 and/or screen dock 404.

In some embodiments a screen dock 404 may be configured to receive and screen a data record containing a request for a patient. In the example embodiment a screen dock 404 such as screen dock 404VL, may be configured to receive such a data record. Upon passing a screen, communication may be sent to a patient with a request for additional information. This request may be sent by an automator 410 upon activation. A screen dock 404 may have an automator 410 associated, in the present example automator 410VL may have an integration, such as an API integration with a communication platform, as an example, Podium, by Podium Corp, Inc, or a similar communication platform.

A data record may remain visible at a screen dock 404 (e.g., 404VL) until additional information has been collected from a patient. Once received, an authorized user may be notified. An authorized user may have specific training in the review of virtual records. If the additional data received is acceptable, a data record may be transferred for review by a healthcare provider.

If after review at data dock 402VD and/or review at screen dock 404VL, an authorized user with training and knowledge in virtual records, reviews and adds the requested approval, the data record may be moved to screen dock 404VJ. If the data passes the screen, an automator 410 may be activated. In the example embodiment, an automator 401VJ may transfer a data record to a different data task station 400. For example, the data record may be moved to data task station 400IV. In addition, automator 410VL may also generate a due date for a data record. For example, if a healthcare provider reviews virtual progress assessments only on certain days, an automator 410VL may be configured to generate a due date which correlates with a designated review day. Automator 410 410VL may also assign a data record to a specific healthcare provider.

In some embodiments, data received, displayed, requested, modified, and/or transferred at a data task station 400IV with the unique header 412 of Provider Review, may all be related to data which may require review by a Provider. As an example, a healthcare facility may receive data records in need of review and feedback by a healthcare provider. In the example embodiment, a data record which passes screening at screen dock 404VJ, may be transferred by an automator to data dock 402IVA of data task station 400IV. An authorized user, such as a healthcare provider, may access this data dock and review the data record.

Data dock 402IVA may be configured to display all relevant information to a healthcare provider to conduct a remote progress review. Data displayed may include, but is not limited to all patient records, all current and past virtual record submissions, treatment notes, a link to view intra-oral scans associated with a patient, and/or a link to view a digital treatment model. Data dock 402IVA may also be configured to display a request for input from a healthcare provider. As an example, this may include any questions received from a patient. Other examples may include what next steps are needed for a patient. Based on the aggregated data within a data record, the request may ask if a patient is ready to complete treatment, it may request timing for next in person visit, etc.

In some embodiments, information may be provided by a laboratory, manufacturer, or medical device company which identifies certain markers to look for during virtual monitoring. For example, a tooth aligning device may have data from the manufacturer highlighting teeth which may be moving. Data may also identify teeth which are not expected to be fully seated within a tooth aligning appliance. This may be identified by unique identifiers, such as colors associated with movement or no movement, and fully seated or space expected.

A healthcare provider may review all relevant data displayed at data dock 402IVA and input requested data. A healthcare provider may move a complete data record to a screen dock 404. In the present embodiment, a data record may be moved to screen dock 404IVB. Screen dock 404IVB may have an automator 410 associated. If the data passes screening against a predetermined data requirement and automator 410IVB is activated, one or more automations may be performed.

An automator 410, such as an automator 410IVB, may transfer a data record to a different data task station 400 or data dock 402. In the example embodiment, a data record may be transferred to data task station 400V. A data dock 402, such as data dock 402VK, may be configured to receive such a data record. Data dock 402VK may display a data record to users authorized to access data dock 402VK.

Before continuing discussion of data task station 400V, one additional example pertaining to data task station 400IV is provided. Another example of how a data task station configured to receive, display, request, modify, and/or transfer data in need of review by a healthcare provider may be used in practice, one may consider laboratory orders. A patient in need of laboratory orders may have a data record displayed at data task station 400IV. In some embodiments more than one screen dock 404 may be associated with an automator 410 configured to transfer a data record to a data dock 402 within data task station 400IV. Different internal and/or external laboratories, different types of treatment, different stages in treatment, are all data which may meet different criteria as a data record moves within and between data task stations 400. The variations in data content may cause each data record to pass through a unique combination of data docks 402 and screen docks 404. As mentioned previously the data input received at the most recent data dock 402 may be the only factor in identifying the next appropriate data dock 402 or screen dock 404. Regardless, of all of the above-mentioned factors, each data record may be transferred to data task station 400IV when the criteria for review have been met. Thus, all data records in need of laboratory order approval by a healthcare provider may pass through a data task station configured to receive, display, request, modify, and/or transfer data records in need of provider review. This facilitates efficient and effective review of laboratory orders for a healthcare provider. A healthcare provider does not need to seek out orders in need of approval, he/she does not need to access multiple sources to find all information needed to approve an order, and all information presented for review may be real time operating information.

In some embodiments, a healthcare provider approval for a laboratory order may have an integration, such as an API or HL7 integration, to notify an external laboratory directly of approval. This may be a direct integration within an external system, or this may be an email notification sent to an external laboratory with approval information.

As those with ordinary skill in the art recognize, such system has an advantage over existing methods in that laboratory orders do not need to pass from a technician to a healthcare provider, back to a technician, and then on to a laboratory. A technician may transfer a laboratory order to a healthcare provider along with all information needed to approve the order. A healthcare provider may review the order and upon approval it may be sent directly to a laboratory for processing.

Returning to discussion of data task station 400V, an authorized with access to data dock 402VK, may review input from a healthcare provider. Based on this data an authorized user may input feedback to provide the patient. A data record may be moved to one or more screen docks 404 of data task station 400V. Where the data record should go may be determined by the data input received at data dock 402VI.

In some embodiments, screen dock 404VN may be accessed when review of virtual records has been completed, and no in-person visit is needed at this time. An authorized user may move a data record displayed at data dock 402VK to screen dock 404VN. If a data record passes screening at screen dock 404VN, automator 410VN may perform one or more automations. For example, automator 410VN may transfer a data record to data dock 402VA. In some embodiments, automator 410VN may also generate a due date. This due date may be configured to coincide with the timing for when an automated reminder should be sent to a patient with a link to complete a next virtual visit.

In some embodiments, the data record visible at data dock 402VA may be accessible by an authorized user with training and skill in virtual monitoring. In some embodiments, a data record displayed at data dock 402VA may have a due date associated. This due date may identify when an automated message should be sent to the specified party in the data record. In some embodiments, when this date arrives, data records may be moved to a screen dock 404 of data task station 400V. As an example, all data records with a due date of today may be visible at the top of a screen dock 404. In some embodiments, settings may be adjusted to only display data records with a due date of today.

An authorized user may be notified of the due date and signaled to move said data records to a screen dock 404. In some embodiments, data records with a current due date may be moved to screen dock 404VB. If a screen is passed and automator 410VB is activated, automator 410VB may perform one or more automations. In some embodiments, a communication platform, such as Podium by Podium Corp, Inc, may be associated with screen dock 404VB via one or more APIs. A data record moved to screen dock 404VB may pass a screen to activate automator 410VB. Automator 410VB may trigger a text communication to a patient containing a link to submit virtual records. Automator 410VB may also modify the due date within a data record. This due date may be generated based on the amount of time before a data record needs to be transferred to data task station 400IV.

In some embodiments, a data record may remain visible at screen dock 404VB First sent until due date arrives. If data content received at data dock 402VD contains an identifier unique to a specified party which matches an identifier within a data record displayed at screen dock 404VB, aggregator 416 may recognize this identifier. If an identifier is recognized, aggregator 416 may add the initial data content received at screen dock 404VD to a data record with the matching identifier which may be visible at screen dock 404VB.

If the due date expires for a data record visible at data dock 402VB, an authorized user may move a data record to screen dock 404VC. If a screen is passed and automator 410VC is activated, automator 410VC may perform one or more automations. A screen dock 404 may have an integration with an external system, for example an API integration with a communication platform. A communication platform, such as Podium by Podium Corp, Inc, may be associated with screen dock 404VC via one or more APIs. A data record moved to screen dock 404VC may pass a screen to activate automator 410VC. Automator 410VC may trigger a text communication to a patient containing a link to submit virtual records. Automator 410VC may also modify the due date within a data record. This due date may be generated based on the amount of time before a data record needs to be transferred to data task station 400IV.

In some embodiments, automated messages may continue to be sent until the requested action has been taken. In some embodiments, data received, displayed, requested, modified, and/or transferred at a particular data task station 400 may be prone to cycle through a series of data docks 402 and screen dock 404 repeatedly until a predetermined data requirement is met. As exemplified in the detailed description of data task station 400V Virtual Monitoring, automated messages may be sent outside the system 1, due dates may be modified, data records may be assigned, and descriptive tags may be added by an automator 410. Incoming data may be received when an activator 414 activates a data content receiver or an authorized user satisfies a data request. Incoming data may be aggregated by an aggregator 416. A data record may continue to aggregate data from the same series of data docks 402 and screen docks 404 until a data requirement is met to pass a different screen. Once a data dock 402 receives data input to satisfy this requirement, a data record may move to a different data dock 402 or screen dock 404 outside of the previous cycle. As those with ordinary skill in the art know, two data records located at the same downstream data dock 402 may contain different amounts and types of data content.

In some embodiments, a data record with a subscription for a service, good, product, or care may cycle through a series a data dock 402 and/or screen docks 404 which may automatically update due dates, trigger order deliveries, and send and receive payment requests and/or notifications.

As data records move within and between data task station 400, data docks 402, and/or screen docks 404, certain inventory may be monitored. For example, a particular embodiment may have a data task station 400 related to vaccine administration. As discussed in reference to data task station 400I, a person may schedule an appointment for vaccination on a web page associated with vaccine delivery locations. A person may access a scheduler to select a location, time, and date. A bounce back email may be sent confirming location, date, and time. This bounce back email may also contain a unique two-dimensional bar code, such as a quick response (QR) code linked to the patient's name, date, time, and location of appointment. In some embodiments, a data dock 402 (e.g., for Vaccine Administration) displayed at a data task station 400 may be configured to receive data content containing patient demographic information and appointment location, time, and date. This data dock 402 may be configured to set a due date of one week before the appointment. This data dock 402 may also be configured to transfer a data record to a screen dock 404 on this due date. A screen dock 404 may screen a data record against a predetermined data requirement, such as the due date. If the screen is passed, an automator 410 may be activated. Automator 410 may trigger communication sent via text and/or email to the contact information contained within a data record. An HL7 and/or API integration may be used as an example to send such a communication. Automator 410 may also update a due date within a data record. This due date may be configured as an appointment date minus one day. Automator 410 may also be configured to transfer a data record to a different screen dock 404 once the requirement of appointment date minus one day is met. This screen dock may screen a data record against a predetermined data requirement. If the requirement is met, such as appointment date minus one day, an automator 410 may be activated. This automator 410 may trigger communication sent via text and/or email to the contact information contained within a data record. An HL7 and/or API integration may be used as an example to send such a communication. Automator 410 may also update a due date within a data record. This new due date may be the appointment date. If a patient arrives for an appointment, the QR code may be scanned upon vaccine delivery. When the QR code is recognized, an activator 414 may activate a data content receiver to receive data. In this example, the received data may include the type, manufacturer, and lot number of the vaccine administered. This content may be received at a screen dock 404 which may have a header 412 identifying the location of vaccine administration. A screen dock 404 which may be configured to receive vaccine information form a specific administration location, may have an automator 410. If a data screen is passed, automator 410 may be activated. Automator 410 may trigger an email and/or text to the specified party within a data record. An email and/or text may be sent using an integration, such as an API and/or HL7 integrations, may send an email containing all of the vaccine information. This screen dock may also be used to track the number of vaccines administered at this location. Computer program 16 may query data logs to track specified metrics. Once a predetermined number of vaccines has been administrated, a metric threshold may be met. This may trigger and email and/or notification within or outside of the system 1 to order additional vaccinations to a specific location.

Any data record which passes thought a data dock 402 or screen dock 404 may be recorded in a log. A query of a data log may produce metrics which may be used to track and reorder inventory.

In some embodiments a data dock may include subscription options for ordering supplies, such as, but not limited to, scanner sleevies, dental adhesives, patient supplies, and the like. A data dock may further include a subscription options for appliance ordering, virtual visit, choose to order next or additional designs of appliance.

As provided above, the present application provides advantages recognized by those with ordinary skill in the art. These advantages include presenting only relevant data to authorized users. Additionally, a unique data request may be displayed only to an authorized user with the training and access to collect and add the requested information. An authorized user may then pass this information along to an Automator. An automator may screen this information against a predetermined data requirement. If the requirement is met the data record may be transferred. The data record may now be visible by a different authorized user. Only the data relevant to this authorized user may be displayed, along with a unique data request. Upon review, an authorized user with training and access to collect the requested information. After completion an authorized user may transfer the data record to an automator. The automator may screen this information against a predetermined data requirement. If the requirement is not met, the data record may remain visible to the authorized user until the appropriate data requirement has been met.

As can be easily understood from the foregoing, the basic concepts of the present disclosure may be embodied in a variety of ways. One or more techniques disclosed herein may involve numerous and varied embodiments of a stackable jewelry system and methods for making and using such a stackable jewelry system.

As such, embodiments or elements of the disclosed herein by the description or shown in the figures or tables accompanying this application are not intended to be limiting, but rather exemplary of the numerous and varied embodiments generically encompassed by the disclosure or equivalents encompassed with respect to any particular element thereof. In addition, the specific description of a single embodiment or element of the disclosure may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this disclosure is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "screen" should be understood to encompass disclosure of the act of "screening"—whether explicitly discussed or not—and, conversely, were there effectively disclosure of the act of "screening", such a disclosure should be understood to encompass disclosure of a "screen" and even a "means for screening". Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present disclosure, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present disclosure, the term "a" or "an" entity refers to one or more of that entity unless otherwise limited. As such, the terms "a" or "an", "one or more" and "at least one" can be used interchangeably herein.

Further, for the purposes of the present disclosure, the term "coupled" or derivatives thereof can mean indirectly coupled, coupled, directly coupled, connected, directly connected, or integrated with, depending upon the embodiment.

Additionally, for the purposes of the present disclosure, the term "integrated" when referring to two or more components means that the components (i) can be united to provide a one-piece construct, a monolithic construct, or a unified whole, or (ii) can be formed as a one-piece construct, a monolithic construct, or a unified whole. Said another way, the components can be integrally formed, meaning connected together so as to make up a single complete piece or unit, or so as to work together as a single complete piece or unit, and so as to be incapable of being easily dismantled without destroying the integrity of the piece or unit.

Thus, the applicant(s) should be understood to claim at least: i) each of the features herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application, if any, provides a statement of the field of endeavor to which the disclosure may pertain. This section may also incorporate or contain paraphrasing of certain United States patents, patent applications, publications, or subject matter of the claimed invention useful in relating information, problems, or concerns about the state of technology to which the disclosure may be drawn toward. It is not intended that any United States patent, patent application, publication, statement or other information cited or incorporated herein be interpreted, construed or deemed to be admitted as prior art with respect to the disclosure.

The claims set forth in this specification, if any, are hereby incorporated by reference as part of this description of the disclosure, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon. The elements following an open transitional phrase such as "comprising" may in the alternative be claimed with a closed transitional phrase such as "consisting essentially of" or "consisting of" whether or not explicitly indicated the description portion of the specification.

Additionally, the claims set forth in this specification, if any, are further intended to describe the metes and bounds of a limited number of embodiments of the disclosure and are not to be construed as the broadest embodiment of the disclosure or a complete listing of embodiments of the disclosure that may be claimed. The applicant does not waive any right to develop further claims based upon the description set forth above as a part of any continuation, division, or continuation-in-part, or similar application.

The invention claimed is:

1. A computer-implemented system for implementing and tracking a healthcare process, comprising:

a processor communicatively coupled to a non-transitory memory containing a computer code, which, when executed by the processor, performs operations comprising:
  initiating a plurality of data task stations, the plurality of data task stations deployed across a plurality of computing systems, the plurality of data task stations linked using one or more interactive connections between the plurality of data task stations, each data task station of the plurality of data task stations associated with at least one party to a healthcare process, wherein the healthcare process is a teeth aligning process;
  enabling a first data task station of the plurality of data task stations on a first computing system of the plurality of computing systems, the first computing system associated with a first party to the healthcare process, the first data task station associated with a first pre-determined data content requirement, wherein the first data task station is associated with at least a first step of the healthcare process;
  enabling a data intake dock of the first data task station to receive a first data content;
screening said first data content against the first pre-determined data content requirement of said first data task station, said screening actuated by movement of said first data content associated to an automator of the data intake dock;
  enabling, by operation of said automator, after said first data content satisfying said screen against said first pre-determined data content requirement, a second data task station of the plurality of data task stations of a second computing system of the plurality of computing systems, the second computing system remote from the first computing system, the second computing system associated with a second party to the healthcare process, the second data task station associated with a second predetermined data content requirement, wherein the second data task station is associated with at least a second step of the healthcare process;
  enabling, by operation of said automator, a second data intake dock of said second data task station to receive the first data content from the first data task station, the second data intake dock of said second data task station having an interactive connection with the first data intake dock of the first data task station, such that the automator of the first data intake dock automatically moves the data content from the first data intake dock to the second data intake dock when the first data content is determined to satisfy the screen against said first pre-determined data content requirement; and
  disabling, by operation of said automator, after said first data content satisfying said screen against said first pre-determined data content requirement, the screen of said first data content of said first data task station.

2. The computer-implemented system of claim 1, wherein the first data task station is associated with a first type of user and wherein the second data task station is associated with a second type of user.

3. The computer-implemented system of claim 1, further comprising:
  screening said second data content against a second pre-determined data content requirement of said second data task station, said screen actuated by movement of said second data content to a second automator site of said second data task station, said second automator site includes a second automator; and
  enabling, by operation of said automator, after said second data content satisfying said screen against said second pre-determined data content requirement, a third data task station of the plurality of data task stations of a third computing system of the plurality of computing systems, the third computing system remote from the first computing system and the second computing system, the third computing system associated with a third party to the healthcare process, the third data task station associated with a third predetermined data content requirement, wherein the third data task station is associated with at least a third step of the healthcare process.

4. The computer-implemented system of claim 1, wherein said first data content and said second data content is aggregated with further pre-determined data content throughout downstream steps of the healthcare process.

5. The computer-implemented system of claim 1, wherein said first data content and said second data content is aggregated with further data content throughout downstream steps of the healthcare process.

6. The computer-implemented system of claim 1, wherein said first data content and said second data content is aggregated with further data content throughout downstream steps of the healthcare process.

7. A computer system having an operating state wherein in said operating state, said computer system is configured to perform operations comprising:
  receiving a first data content at a first data intake dock of a first data task station displayed via a first computing system;
  screening the first data content against a first pre-determined data content requirement of the first data intake dock, said screen actuated by movement of said first data content to an automator of the data intake dock, wherein the first data task station is associated with a first step of a healthcare process;
  enabling, by operation of said automator, after said first data content satisfying said screen against said first pre-determined data content requirement, a second data task station displayed via a second computing system, the second data task station comprising a second data intake dock associated with a second predetermined data content requirement, wherein the second data task station is associated with a second step of the healthcare process;
  enabling, by operation of said automator, the second data task station to receive the data content from the first data task station through the second data intake dock, the second data intake dock having an interactive connection with the first data intake dock of the first data task station, such that the automator of the first data intake dock automatically moves the data content from the first data intake dock to the second data intake dock when the first data content is determined to satisfy the screen against said first pre-determined data content requirement; and
  disabling, by operation of said automator, after said first data content satisfying said screen against said first pre-determined data content requirement, the screen of said first data content of said first data task station.

8. The computer system of claim 7, wherein the first data task station is associated with a first type of user and wherein the second data task station is associated with a second type of user.

9. The computer system of claim 7, further comprising:
screening a second data content against a second predetermined data content requirement of the second data task station, said screen actuated by movement of said second data content of said second data task station to a second automator of the second data intake dock; and
enabling, by operation of said second automator, after said second data content satisfying said screen against said second pre-determined data content requirement, a third data task station displayed via a third computing system, the third data task station associated with a third predetermined data content requirement, wherein the third data task station is associated with a third step of the healthcare process.

10. The computer system of claim 7, wherein the first data task station is associated with a first type of user and wherein the second data task station is associated with a second type of user.

11. The computer system of claim 7, further comprising:
screening a second data content against a second predetermined data content requirement of the second data task station, said screen actuated by movement of said second data content of said second data task station to a second automator of the second data intake dock; and
enabling, by operation of said second automator, after said second data content satisfying said screen against said second pre-determined data content requirement, a third data task station displayed via a third computing system, the third data task station associated with a third predetermined data content requirement, wherein the third data task station is associated with a third step of the healthcare process.

12. A method in a computer implemented system, comprising:
initiating a plurality of data task stations, the plurality of data task stations deployed across a plurality of computing systems, the plurality of data task stations linked using one or more interactive connections between the plurality of data task stations, each data task station of the plurality of data task stations associated with at least one party to a healthcare process, wherein the healthcare process is a teeth aligning process;
enabling a first data task station of the plurality of data task stations on a first computing system of the plurality of computing systems, the first computing system associated with a first party to the healthcare process, the first data task station associated with a first pre-determined data content requirement;
enabling a data intake dock of said first data task station to receive, a first data content, wherein the first data task station is associated with a first step of a healthcare process;
screening said first data content against the first pre-determined data content requirement of said first data task station, said screen actuated by movement of said first data content to an automator of the data intake dock;
enabling, by operation of said automator, after said first data content satisfying said screen against said first pre-determined data content requirement, a second data task station of the plurality of data task stations of a second computing system of the plurality of computing systems, the second computing system remote from the first computing system, the second computing system associated with a second party to the healthcare process, the second data task station associated with a second predetermined data content requirement, wherein the second data task station is associated with a second step of the healthcare process;
enabling, by operation of said automator, a second data intake dock of said second data task station to receive the data content from the first data task station, the second data intake dock of said second data task station having an interactive connection with the first data intake dock of the first data task station, such that the automator of the first data intake dock automatically moves the data content from the first data intake dock to the second data intake dock when the first data content is determined to satisfy the screen against said first pre-determined data content requirement; and
disabling, by operation of said automator, after said first data content satisfying said screen against said first pre-determined data content requirement, the screen of said first data content of said first data task station.

13. The method of claim 12, wherein the first data task station is associated with a first type of user and wherein the second data task station is associated with a second type of user.

14. The method of claim 12, further comprising:
screening said second data content against the second pre-determined data content requirement of said second data task station, said screen actuated by movement of said second data content associated to a second automator site of said second data task station, said second automator site includes a second automator; and
enabling, by operation of said automator, after said second data content satisfying said screen against said second pre-determined data content requirement, a third data task station of the plurality of data task stations of a third computing system of the plurality of computing systems, the third computing system remote from the first computing system and the second computing system, the third computing system associated with a third party to the healthcare process, the third data task station associated with a third predetermined data content requirement, wherein the third data task station is associated with at least a third step of the healthcare process.

15. The method of claim 12, wherein said first data content and said second data content is aggregate with further pre-determined data content throughout downstream steps of the healthcare process.

16. A computer implemented method comprising:
receiving a first data content at a first data intake dock of a first data task station displayed via a first computing system;
screening the first data content against a first pre-determined data content requirement of the first data intake dock, said screen actuated by movement of said first data content to an automator of the data intake dock, wherein the first data task station is associated with a first step of a healthcare process;
enabling, by operation of said automator, after said first data content satisfying said screen against said first pre-determined data content requirement, a second data task station displayed via a second computing system, the second data task station comprising a second data intake dock associated with a second predetermined data content requirement, wherein the second data task station is associated with a second step of the healthcare process;
enabling, by operation of said automator, the second data task station to receive the data content from the first data task station through the second data intake dock, the second data intake dock having an interactive connection with the first data intake dock of the first data task station, such that the automator of the first data intake dock automatically moves the data content from the first data intake dock to the second data intake dock when the first data content is determined to satisfy the screen against said first pre-determined data content requirement; and disabling, by operation of said automator, after said first data content satisfying said screen against said first pre-determined data content requirement, the screen of said first data content of said first data task station.

\* \* \* \* \*